(12) United States Patent
Gertler et al.

(10) Patent No.: US 6,716,597 B2
(45) Date of Patent: Apr. 6, 2004

(54) METHODS AND PRODUCTS FOR REGULATING CELL MOTILITY

(75) Inventors: Frank B. Gertler, Boston, MA (US); James E. Bear, Brighton, MA (US); Joseph J. Loureiro, Cambridge, MA (US); Jurgen Wehland, Bad Harzburg (DE)

(73) Assignee: Massachusetts Institute of Technology, Cambridge, MA (US)

(*) Notice: Subject to any disclaimer, the term of this patent is extended or adjusted under 35 U.S.C. 154(b) by 226 days.

(21) Appl. No.: 09/823,240

(22) Filed: Mar. 30, 2001

(65) Prior Publication Data

US 2002/0048813 A1 Apr. 25, 2002

Related U.S. Application Data

(60) Provisional application No. 60/194,564, filed on Apr. 3, 2000.

(51) Int. Cl.[7] .............................................. C12Q 1/02
(52) U.S. Cl. ......................................................... 435/29
(58) Field of Search ........................................... 435/29

(56) References Cited

U.S. PATENT DOCUMENTS

| | | |
|---|---|---|
| 5,851,786 A | 12/1998 | Johnson |
| 5,912,128 A | 6/1999 | Lal et al. |
| 5,928,882 A | 7/1999 | Sabo et al. |
| 5,935,850 A * | 8/1999 | Clark et al. ................ 435/325 |
| 5,976,819 A | 11/1999 | Finkel et al. |
| 5,990,087 A | 11/1999 | Lal et al. |

FOREIGN PATENT DOCUMENTS

| | | |
|---|---|---|
| WO | WO 98/01755 A1 | 1/1998 |
| WO | WO 99/24052 A2 | 5/1999 |
| WO | US01/10249 | 3/2001 |
| WO | WO 01/74378 A2 | 10/2001 |

OTHER PUBLICATIONS

Carl, U.D. et al., "Aromatic and basic residues within the EVH1 domain of VASP specify its interation with proline–rich ligands", Current Biology, 1999, pp. 715–718, vol. 9, Elsevier Science Ltd.

Drees, B.E. et al., "Molecular Dissection of Zyxin Function Reveals Its Involvement in Cell Motility", The Journal of Cell Biology, Dec. 27, 1999, pp. 1549–1559, vol. 147, No. 7, The Rockefeller University Press.

Fedorov, A.A. et al., "Structure of EVH1, a novel proline–rich ligand–binding module involved in cytoskeletal dynamics and neural function", Nature Structural Biology, Jul. 1999, p. 661–665, vol. 6, No. 7.

Laurent, V. et al., "Role of Proteins of the Ena/VASP Family in Actin–based Motility of Listeria monocytogenes", The Journal of Cell Biology, Mar. 22, 1999, pp. 1245–1258, vol. 144, No. 6, The Rockefeller University Press.

Niebuhr, K. et al., "A novel proline–rich motif present in ActA of Listeria monocytogenes and cytoskeletal proteins is the ligand for the EVH1 domain, a protein module present in the Ena/VASP family", The EMBO Journal, 1997, pp. 5433–5444, vol. 16, No. 17, Oxford University Press.

Bear, J.E. et al., "Antagonism between Ena/VASP Proteins and Actin Filament Capping Regulates Fibroblast Motility", Cell, May 17, 2002, pp. 1–13, vol. 109, Cell Press.

Goh, K. L. et al., "Ena/VASP Proteins Regulate Cortical Neuronal Positioning", Current Biology, Apr. 2, 2002, pp. 565–569, vol. 12, Elsevier Science Ltd.

Aszodi, A. et al. "The vasodilator–stimulated phosphoprotein (VASP) is involved in cGMP– and cAMP– mediated inhibition of agonist–induced platelet aggregation, but is dispensable for smooth muscle function", The EMBO Journal, 1999, pp. 37–48, vol. 18, No. 1, European Molecular Biology Organization.

Bear, J.E. et al., "Negative Regulation of Fibroblast Motility by Ena/VASP Proteins", Cell, Jun. 23, 2000, pp. 717–728, vol. 101, Cell Press.

Gertler, F.B. et al., "Mena, a Relative of VASP and Drosophila Enabled, is Implicated in the Control of Microflament Dynamics", Cell, Oct. 18, 1996, pp. 227–239, vol. 87, Cell Press.

Hauser, W. et al., "Megakaryocyte hyperplasia and enhanced agonist–induced platelet activation in vasodilator–stimulated phosphoprotein knockout mice", Proc. Natl. Acad. Sci. USA, Jul. 1999, pp. 8120–8125, vol. 96.

Krause. M. et al., "Fyn–binding Protein (Fyb)SLP–76–associated Protein (SLAP), Ena/Vasodilator––stimulated Phosphoprotein (VASP) Proteins and the Arp2/3 Complex Link T Cell Receptor (TCR) Signalinng to the Actin Cytoskeleton", The Journal of Cell Biology, Apr. 3, 2000, pp. 181–194, vol. 149, No. 1, The Rockefeller University Press.

Liu, K. et al., "Reversible Tumorigenesis Induced by Deficiency of Vasodilator–Stimulated Phosphoprotein", Molecular and Cellular Biology, May 1999, pp. 3696–3703, vol. 19, No. 5, American Society for Microbiolgy.

Machesky, L.M., "Putting on the Brakes: A Negative Regulatory Function for Ena/VASP Proteins in Cell Migration", Cell, Jun. 23, 2000, pp. 685–688, vol. 101, Cell Press.

Reinhard, M. et al., "Actin–based motility: stop and go with Ena/VASP proteins", Trends in Biochemical Sciences, Apr. 2001, pp. 243–249, vol. 26, No. 4.

* cited by examiner

Primary Examiner—Terry McKelvey
(74) Attorney, Agent, or Firm—Wolf, Greenfield & Sacks, P.C.

(57) ABSTRACT

The invention relates to methods for regulating cell motility and related products. In particular methods for promoting and preventing cell migration are described herein. The methods have a variety of clinical, diagnostic and therapeutic uses, e.g., for wound healing, tissue generation, and treatment and prevention of neurodegenerative disease and metastasis.

7 Claims, 11 Drawing Sheets

SEQUENCE LISTING

<160> NUMBER OF SEQ ID NOS: 11

<210> SEQ ID NO 1
<211> LENGTH: 10
<212> TYPE: PRT
<213> ORGANISM: Listeria monocytogenes
<220> FEATURE:
<221> NAME/KEY: UNSURE
<222> LOCATION: (1)...(1)
<223> OTHER INFORMATION: Xaa is Asp or Glu
<221> NAME/KEY: UNSURE
<222> LOCATION: (7)...(7)
<223> OTHER INFORMATION: Xaa is any amino acid

<400> SEQUENCE: 1

Xaa Phe Pro Pro Pro Xaa Asp Asp Glu
 1               5                   10

<210> SEQ ID NO 2
<211> LENGTH: 802
<212> TYPE: PRT
<213> ORGANISM: Mus musculus

<400> SEQUENCE: 2

Met Ser Glu Gln Ser Ile Cys Gln Ala Arg Ala Ala Val Met Val Tyr
 1               5                  10                  15

Asp Asp Ala Asn Lys Lys Trp Val Pro Ala Gly Gly Ser Thr Gly Phe
                20                  25                  30

Ser Arg Val His Ile Tyr His His Thr Gly Asn Asn Thr Phe Arg Val
            35                  40                  45

Val Gly Arg Lys Ile Gln Asp His Gln Val Val Ile Asn Cys Ala Ile
        50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95

Ala Asn Val Phe Ala Ser Ala Met Met His Ala Leu Glu Val Leu Asn
                100                 105                 110

Ser Gln Glu Ala Ala Gln Ser Lys Val Thr Ala Thr Gln Asp Ser Thr
            115                 120                 125

Asn Leu Arg Cys Ile Phe Cys Gly Pro Thr Leu Pro Arg Gln Asn Ser
        130                 135                 140

Gln Leu Pro Ala Gln Val Gln Asn Gly Pro Ser Gln Glu Glu Leu Glu
145                 150                 155                 160

Ile Gln Arg Arg Gln Leu Gln Glu Gln Arg Gln Lys Glu Leu Glu
                165                 170                 175

Arg Glu Arg Met Glu Arg Glu Arg Leu Glu Arg Glu Arg Leu Glu Arg
                180                 185                 190

Glu Arg Leu Glu Arg Glu Arg Leu Glu Gln Glu Gln Leu Glu Arg Gln
            195                 200                 205

Arg Gln Glu Arg Glu His Val Glu Arg Leu Glu Arg Glu Arg Leu Glu
        210                 215                 220

Arg Leu Glu Arg Glu Arg Gln Arg Glu Arg Glu Arg Leu Glu Gln
225                 230                 235                 240

Leu Glu Arg Glu Gln Val Glu Trp Glu Arg Glu Arg Arg Met Ser Asn
                245                 250                 255

Ala Ala Pro Ser Ser Asp Ser Ser Leu Ser Ser Ala Pro Leu Pro Glu

-continued

```
                260                 265                 270
Tyr Ser Ser Cys Gln Pro Pro Ser Ala Pro Pro Ser Tyr Ala Lys
        275                 280                 285
Val Ile Ser Ala Pro Val Ser Asp Ala Thr Pro Asp Tyr Ala Val Val
290                 295                 300
Thr Ala Leu Pro Pro Thr Ser Thr Pro Pro Thr Pro Pro Leu Arg His
305                 310                 315                 320
Ala Ala Thr Arg Phe Ala Thr Ser Leu Gly Ser Ala Phe His Pro Val
                325                 330                 335
Leu Pro His Tyr Ala Thr Val Pro Arg Pro Leu Asn Lys Asn Ser Arg
        340                 345                 350
Pro Ser Ser Pro Val Asn Thr Pro Ser Ser Gln Pro Pro Ala Ala Lys
        355                 360                 365
Ser Cys Ala Trp Pro Thr Ser Asn Phe Ser Pro Leu Pro Pro Ser Pro
        370                 375                 380
Pro Ile Met Ile Ser Ser Pro Pro Gly Lys Ala Thr Gly Pro Arg Pro
385                 390                 395                 400
Val Leu Pro Val Cys Val Ser Ser Pro Val Pro Gln Met Pro Pro Ser
                405                 410                 415
Pro Thr Ala Pro Asn Gly Ser Leu Asp Ser Val Thr Tyr Pro Val Ser
                420                 425                 430
Pro Pro Pro Thr Ser Gly Pro Ala Ala Pro Pro Pro Pro Pro Pro Pro
                435                 440                 445
Pro Pro Pro Pro Pro Pro Pro Leu Pro Pro Pro Pro Leu Pro Pro
        450                 455                 460
Leu Ala Ser Leu Ser His Cys Gly Ser Gln Ala Ser Pro Pro Gly
465                 470                 475                 480
Thr Pro Leu Ala Ser Thr Pro Ser Ser Lys Pro Ser Val Leu Pro Ser
                485                 490                 495
Pro Ser Ala Gly Ala Pro Ala Ser Ala Glu Thr Pro Leu Asn Pro Glu
            500                 505                 510
Leu Gly Asp Ser Ser Ala Ser Glu Pro Gly Leu Gln Ala Ala Ser Gln
        515                 520                 525
Pro Ala Glu Ser Pro Thr Pro Gln Gly Leu Val Leu Gly Pro Pro Ala
        530                 535                 540
Pro Pro Pro Pro Pro Leu Pro Ser Gly Pro Ala Tyr Ala Ser Ala
545                 550                 555                 560
Leu Pro Pro Pro Gly Pro Pro Pro Pro Pro Leu Pro Ser Thr
                565                 570                 575
Gly Pro Pro Pro Pro Pro Pro Pro Pro Leu Pro Asn Gln Ala
        580                 585                 590
Pro Pro Pro Pro Pro Pro Pro Ala Pro Pro Leu Pro Ala Ser Gly
        595                 600                 605
Ile Phe Ser Gly Ser Thr Ser Glu Asp Asn Arg Pro Leu Thr Gly Leu
        610                 615                 620
Ala Ala Ala Ile Ala Gly Ala Lys Leu Arg Lys Val Ser Arg Val Glu
625                 630                 635                 640
Asp Gly Ser Phe Pro Gly Gly Gly Asn Thr Gly Ser Val Ser Leu Ala
                645                 650                 655
Ser Ser Lys Ala Asp Ala Gly Arg Gly Asn Gly Pro Leu Pro Leu Gly
                660                 665                 670
Gly Ser Gly Leu Met Glu Glu Met Ser Ala Leu Leu Ala Arg Arg Arg
        675                 680                 685
```

```
Arg Ile Ala Glu Lys Gly Ser Thr Ile Glu Thr Glu Gln Lys Glu Asp
        690                 695                 700
Arg Asn Glu Asp Ala Glu Pro Ile Thr Ala Lys Ala Pro Ser Thr Ser
705                 710                 715                 720
Thr Pro Glu Pro Thr Arg Lys Pro Trp Glu Arg Thr Asn Thr Met Asn
                725                 730                 735
Gly Ser Lys Ser Pro Val Ile Ser Arg Pro Lys Ser Thr Pro Ser Ser
                740                 745                 750
Gln Pro Ser Ala Asn Gly Val Gln Thr Glu Gly Leu Asp Tyr Asp Arg
                755                 760                 765
Leu Lys Gln Asp Ile Leu Asp Glu Met Arg Lys Glu Leu Ala Lys Leu
        770                 775                 780
Lys Glu Glu Leu Ile Asp Ala Ile Arg Gln Glu Leu Ser Lys Ser Asn
785                 790                 795                 800
Thr Ala

<210> SEQ ID NO 3
<211> LENGTH: 5
<212> TYPE: PRT
<213> ORGANISM: Listeria monocytogenes

<400> SEQUENCE: 3

Phe Pro Pro Pro Pro
 1               5

<210> SEQ ID NO 4
<211> LENGTH: 5
<212> TYPE: PRT
<213> ORGANISM: Listeria monocytogenes

<400> SEQUENCE: 4

Ala Pro Pro Pro Pro
 1               5

<210> SEQ ID NO 5
<211> LENGTH: 639
<212> TYPE: PRT
<213> ORGANISM: Listeria monocytogenes

<400> SEQUENCE: 5

Met Gly Leu Asn Arg Phe Met Arg Ala Met Met Val Val Phe Ile Thr
 1               5                  10                  15
Ala Asn Cys Ile Thr Ile Asn Pro Asp Ile Ile Phe Ala Ala Thr Asp
                20                  25                  30
Ser Glu Asp Ser Ser Leu Asn Thr Asp Glu Trp Glu Glu Lys Thr
                35                  40                  45
Glu Glu Gln Pro Ser Glu Val Asn Thr Gly Pro Arg Tyr Glu Thr Ala
        50                  55                  60
Arg Glu Val Ser Ser Arg Asp Ile Lys Glu Leu Glu Lys Ser Asn Lys
65                  70                  75                  80
Val Arg Asn Thr Asn Lys Ala Asp Leu Ile Ala Met Leu Lys Glu Lys
                85                  90                  95
Ala Glu Lys Gly Pro Asn Ile Asn Asn Asn Ser Glu Gln Thr Glu
                100                 105                 110
Asn Ala Ala Ile Asn Glu Glu Ala Ser Gly Ala Asp Arg Pro Ala Ile
        115                 120                 125
Gln Val Glu Arg Arg His Pro Gly Leu Pro Ser Asp Ser Ala Ala Glu
```

```
                130                 135                 140
Ile Lys Lys Arg Arg Lys Ala Ile Ala Ser Ser Asp Ser Glu Leu Glu
145                 150                 155                 160

Ser Leu Thr Tyr Pro Asp Lys Pro Thr Lys Val Asn Lys Lys Lys Val
                165                 170                 175

Ala Lys Glu Ser Val Ala Asp Ala Ser Glu Ser Asp Leu Asp Ser Ser
            180                 185                 190

Met Gln Ser Ala Asp Glu Ser Ser Pro Gln Pro Leu Lys Ala Asn Gln
            195                 200                 205

Gln Pro Phe Phe Pro Lys Val Phe Lys Lys Ile Lys Asp Ala Gly Lys
        210                 215                 220

Trp Val Arg Asp Lys Ile Asp Glu Asn Pro Glu Val Lys Lys Ala Ile
225                 230                 235                 240

Val Asp Lys Ser Ala Gly Leu Ile Asp Gln Leu Leu Thr Lys Lys Lys
                245                 250                 255

Ser Glu Glu Val Asn Ala Ser Asp Phe Pro Pro Pro Thr Asp Glu
            260                 265                 270

Glu Leu Arg Leu Ala Leu Pro Glu Thr Pro Met Leu Leu Gly Phe Asn
        275                 280                 285

Ala Pro Ala Thr Ser Glu Pro Ser Ser Phe Glu Phe Pro Pro Pro
290                 295                 300

Thr Asp Glu Glu Leu Arg Leu Ala Leu Pro Glu Thr Pro Met Leu Leu
305                 310                 315                 320

Gly Phe Asn Ala Pro Ala Thr Ser Glu Pro Ser Ser Phe Glu Phe Pro
                325                 330                 335

Pro Pro Thr Glu Asp Glu Leu Glu Ile Ile Arg Glu Thr Ala Ser
            340                 345                 350

Ser Leu Asp Ser Ser Phe Thr Arg Gly Asp Leu Ala Ser Leu Arg Asn
            355                 360                 365

Ala Ile Asn Arg His Ser Gln Asn Phe Ser Asp Phe Pro Pro Ile Pro
        370                 375                 380

Thr Glu Glu Glu Leu Asn Gly Arg Gly Gly Arg Pro Thr Ser Glu Glu
385                 390                 395                 400

Phe Ser Ser Leu Asn Ser Gly Asp Phe Thr Asp Asp Glu Asn Ser Glu
                405                 410                 415

Thr Thr Glu Glu Glu Ile Asp Arg Leu Ala Asp Leu Arg Asp Arg Gly
            420                 425                 430

Thr Gly Lys His Ser Arg Asn Ala Gly Phe Leu Pro Leu Asn Pro Phe
        435                 440                 445

Ala Ser Ser Pro Val Pro Ser Leu Ser Pro Lys Val Ser Lys Ile Ser
        450                 455                 460

Ala Pro Ala Leu Ile Ser Asp Ile Thr Lys Lys Thr Pro Phe Lys Asn
465                 470                 475                 480

Pro Ser Gln Pro Leu Asn Val Phe Asn Lys Lys Thr Thr Lys Thr
            485                 490                 495

Val Thr Lys Lys Pro Thr Pro Val Lys Thr Ala Pro Lys Leu Ala Glu
                500                 505                 510

Leu Pro Ala Thr Lys Pro Gln Glu Thr Val Leu Arg Glu Asn Lys Thr
            515                 520                 525

Pro Phe Ile Glu Lys Gln Ala Glu Thr Asn Lys Gln Ser Ile Asn Met
        530                 535                 540

Pro Ser Leu Pro Val Ile Gln Lys Glu Ala Thr Glu Ser Asp Lys Glu
545                 550                 555                 560
```

```
Glu Met Lys Pro Gln Thr Glu Glu Lys Met Val Glu Ser Glu Ser
                565                 570                 575

Ala Asn Asn Ala Asn Gly Lys Asn Arg Ser Ala Gly Ile Glu Glu Gly
            580                 585                 590

Lys Leu Ile Ala Lys Ser Ala Glu Asp Glu Lys Ala Lys Glu Glu Pro
        595                 600                 605

Gly Asn His Thr Thr Leu Ile Leu Ala Met Leu Ala Ile Gly Val Phe
        610                 615                 620

Ser Leu Gly Ala Phe Ile Lys Ile Ile Gln Leu Arg Lys Asn Asn
625                 630                 635

<210> SEQ ID NO 6
<211> LENGTH: 4
<212> TYPE: PRT
<213> ORGANISM: Homo sapien
<220> FEATURE:
<221> NAME/KEY: UNSURE
<222> LOCATION: (4)...(4)
<223> OTHER INFORMATION: Xaa is any amino acid

<400> SEQUENCE: 6

Cys Ala Ala Xaa
1

<210> SEQ ID NO 7
<211> LENGTH: 9
<212> TYPE: PRT
<213> ORGANISM: Homo sapien
<220> FEATURE:
<221> NAME/KEY: UNSURE
<222> LOCATION: (9)...(9)
<223> OTHER INFORMATION: Xaa is any amino acid

<400> SEQUENCE: 7

Phe Pro Pro Pro Pro Cys Ala Ala Xaa
1               5

<210> SEQ ID NO 8
<211> LENGTH: 9
<212> TYPE: PRT
<213> ORGANISM: Homo sapien
<220> FEATURE:
<221> NAME/KEY: UNSURE
<222> LOCATION: (9)...(9)
<223> OTHER INFORMATION: Xaa is any amino acid

<400> SEQUENCE: 8

Ala Pro Pro Pro Pro Cys Ala Ala Xaa
1               5

<210> SEQ ID NO 9
<211> LENGTH: 684
<212> TYPE: PRT
<213> ORGANISM: Drosophila melanogaster

<400> SEQUENCE: 9

Met Thr Glu Gln Ser Ile Ile Gly Ala Arg Ala Ser Val Met Val Tyr
1               5                   10                  15

Asp Asp Asn Gln Lys Lys Trp Val Pro Ser Gly Ser Ser Ser Gly Leu
            20                  25                  30

Ser Lys Val Gln Ile Tyr His His Gln Gln Asn Asn Thr Phe Arg Val
        35                  40                  45

Val Gly Arg Lys Leu Gln Asp His Glu Val Val Ile Asn Cys Ser Ile
```

```
              50                  55                  60
Leu Lys Gly Leu Lys Tyr Asn Gln Ala Thr Ala Thr Phe His Gln Trp
 65                  70                  75                  80

Arg Asp Ser Lys Phe Val Tyr Gly Leu Asn Phe Ser Ser Gln Asn Asp
                 85                  90                  95

Ala Glu Asn Phe Ala Arg Ala Met Met His Ala Leu Glu Val Leu Ser
                100                 105                 110

Gly Arg Val Ala Asn Asn Pro Gly Gly Pro Pro Thr Asn Gly Asn Gly
                115                 120                 125

Tyr Glu Glu Asp Met Gly Tyr Arg Thr Met Thr Ser Glu Asp Ala Ala
130                 135                 140

Ile Leu Arg Gln Asn Asn Ser Ile Gly Gly His Val Thr Pro Ser Ala
145                 150                 155                 160

Gln Thr Pro Thr Ser Gln Thr Asn Gln Asn Asn Ile Pro Gln Ser Pro
                165                 170                 175

Pro Thr Pro Gln Gly His His Arg Thr Ser Ser Ala Pro Pro Ala Pro
                180                 185                 190

Gln Pro Gln Gln Gln Gln Gln Gln Ala Gln Gln Met Gly Gln
                195                 200                 205

Pro Gly Ser His Tyr Gly Pro Thr Gly Asn Gly Pro Thr Ser Asn Gly
                210                 215                 220

Leu Pro Gln Gln Val Asn Ser Gln Ile Pro Pro Ala Pro Gln Gln Gln
225                 230                 235                 240

Pro Gln Gln Gln Gln Phe Gln Gln Gln Gln Gln Gln Gln Tyr Gln
                245                 250                 255

Gln Met Val Gln Ala Gly Tyr Ala Pro Ser Gln Gln Tyr Gln Gln Pro
                260                 265                 270

His Tyr Val Leu Ser Asn Ser Asn Pro Asn Leu Thr Val His Gln Tyr
                275                 280                 285

Pro Thr Gln Gln Ala Gln Gln Gln Pro Pro Gln Ala Pro Gln Pro Pro
                290                 295                 300

Leu Gln Asn Gly Gly Met Tyr Met Val Gly His Ser His Leu Pro Ser
305                 310                 315                 320

Ser Ala Ser Ala Asn Ser Val Val Tyr Ala Ser Gln Gln Gln Met Leu
                325                 330                 335

Pro Gln Ala His Pro Gln Ala Pro Gln Ala Pro Thr Met Pro Gly Pro
                340                 345                 350

Gly Tyr Gly Gly Pro Pro Val Pro Pro Gln Gln Gln Ala Glu Asn
                355                 360                 365

Pro Tyr Gly Gln Val Pro Met Pro Pro Met Asn Pro Ser Gln Gln
                370                 375                 380

Gln Gln Pro Gly Gln Val Pro Leu Asn Arg Met Ser Ser Gln Gly Gly
385                 390                 395                 400

Pro Gly Gly Pro Pro Ala Pro Ala Pro Pro Pro Pro Pro Pro Ser Phe
                405                 410                 415

Gly Gly Ala Ala Gly Gly Pro Pro Pro Ala Pro Gln Met
                420                 425                 430

Phe Asn Gly Ala Pro Pro Pro Ala Met Gly Gly Pro Pro
                435                 440                 445

Ala Pro Pro Ala Pro Pro Ala Met Gly Gly Pro Pro Ala Pro
                450                 455                 460

Gly Gly Pro Gly Ala Pro Pro Pro Pro Pro Pro Gly Leu Gly
465                 470                 475                 480
```

-continued

```
Gly Ala Pro Lys Lys Glu Asp Pro Gln Ala Asp Leu Met Gly Ser Leu
                485                 490                 495

Ala Ser Gln Leu Gln Gln Phe Lys Leu Lys Lys Asn Lys Val Thr Thr
            500                 505                 510

Ser Ala Pro Glu Asn Ser Gly Ser Ser Thr Ser Ser Gly Gly Ser Gly
            515                 520                 525

Asn Tyr Gly Thr Ile Gly Arg Ser Ser Asn Gly Met Ala Ser Met Met
        530                 535                 540

Asp Glu Met Ala Lys Thr Leu Ala Arg Arg Ala Gln Ala Glu Lys
545                 550                 555                 560

Lys Asp Pro Asp Pro Glu Ala Glu Val Lys Lys Arg Pro Trp Glu Lys
                565                 570                 575

Ser Asn Thr Leu Pro His Lys Leu Ser Gly Ala Gly Ser Gly Ser
            580                 585                 590

Ala Gly Ser Gly His Glu Gly Ala Asn Gly Asn Ser Gly Gly Ala Gly
        595                 600                 605

Ser Asn Thr Thr Asn Ser Gly Gly Glu Ser Pro Arg Pro Met Arg Lys
        610                 615                 620

Arg Phe Gly Ser Ala Ser Glu Glu Thr Ile Leu Lys Val Asn Gly Asp
625                 630                 635                 640

Gly Leu Ser Leu Ala Leu Ser Asn Gly Asp Leu Asp Thr Leu Lys Ala
                645                 650                 655

Glu Ile Val Arg Glu Met Arg Leu Glu Ile Gln Lys Val Lys Asn Glu
                660                 665                 670

Ile Ile Asp Ala Ile Lys Ser Glu Phe Asn Arg Arg
            675                 680

<210> SEQ ID NO 10
<211> LENGTH: 380
<212> TYPE: PRT
<213> ORGANISM: Homo sapien

<400> SEQUENCE: 10

Met Ser Glu Thr Val Ile Cys Ser Ser Arg Ala Thr Val Met Leu Tyr
 1               5                  10                  15

Asp Asp Gly Asn Lys Arg Trp Leu Pro Ala Gly Thr Gly Pro Gln Ala
            20                  25                  30

Phe Ser Arg Val Gln Ile Tyr His Asn Pro Thr Ala Asn Ser Phe Arg
        35                  40                  45

Val Val Gly Arg Lys Met Gln Pro Asp Gln Gln Val Val Ile Asn Cys
    50                  55                  60

Ala Ile Val Arg Gly Val Lys Tyr Asn Gln Ala Thr Pro Asn Phe His
65                  70                  75                  80

Gln Trp Arg Asp Ala Arg Gln Val Trp Gly Leu Asn Phe Gly Ser Lys
                85                  90                  95

Glu Asp Ala Ala Gln Phe Ala Ala Gly Met Ala Ser Ala Leu Glu Ala
            100                 105                 110

Leu Glu Gly Gly Gly Pro Pro Pro Pro Ala Leu Pro Thr Trp Ser
        115                 120                 125

Val Pro Asn Gly Pro Ser Pro Glu Glu Val Glu Gln Gln Lys Arg Gln
    130                 135                 140

Gln Pro Gly Pro Ser Glu His Ile Glu Arg Arg Val Ser Asn Ala Gly
145                 150                 155                 160

Gly Pro Pro Ala Pro Pro Ala Gly Gly Pro Pro Pro Pro Gly Pro
```

-continued

```
                165                 170                 175
Pro Pro Pro Pro Gly Pro Pro Pro Pro Gly Leu Pro Pro Ser Gly
            180                 185                 190

Val Pro Ala Ala Ala His Gly Ala Gly Gly Pro Pro Ala Pro
        195                 200                 205

Pro Leu Pro Ala Ala Gln Gly Pro Gly Gly Gly Ala Gly Ala Pro
        210                 215                 220

Gly Leu Ala Ala Ala Ile Ala Gly Ala Lys Leu Arg Lys Val Ser Lys
225                 230                 235                 240

Gln Glu Glu Ala Ser Gly Gly Pro Thr Ala Pro Lys Ala Glu Ser Gly
                245                 250                 255

Arg Ser Gly Gly Gly Leu Met Glu Glu Met Asn Ala Met Leu Ala
                260                 265                 270

Arg Arg Arg Lys Ala Thr Gln Val Gly Glu Lys Thr Pro Lys Asp Glu
            275                 280                 285

Ser Ala Asn Gln Glu Glu Pro Glu Ala Arg Val Pro Ala Gln Ser Glu
            290                 295                 300

Ser Val Arg Arg Pro Trp Glu Lys Asn Ser Thr Thr Leu Pro Arg Met
305                 310                 315                 320

Lys Ser Ser Ser Val Thr Thr Ser Glu Thr Gln Pro Cys Thr Pro
                325                 330                 335

Ser Ser Ser Asp Tyr Ser Asp Leu Gln Arg Val Lys Gln Glu Leu Leu
                340                 345                 350

Glu Glu Val Lys Lys Glu Leu Gln Lys Val Lys Glu Glu Ile Ile Glu
                355                 360                 365

Ala Phe Val Gln Glu Leu Arg Lys Arg Gly Ser Pro
            370                 375                 380

<210> SEQ ID NO 11
<211> LENGTH: 393
<212> TYPE: PRT
<213> ORGANISM: Mus musculus

<400> SEQUENCE: 11

Met Ser Glu Gln Ser Ile Cys Gln Ala Arg Ala Ser Val Met Val Tyr
1               5                   10                  15

Asp Asp Thr Ser Lys Lys Trp Val Pro Ile Lys Pro Gly Gln Gln Gly
                20                  25                  30

Phe Ser Arg Ile Asn Ile Tyr His Asn Thr Ala Ser Ser Thr Phe Arg
            35                  40                  45

Val Val Gly Val Lys Leu Gln Asp Gln Gln Val Ile Asn Tyr Ser
        50                  55                  60

Ile Val Lys Gly Leu Lys Tyr Asn Gln Ala Thr Pro Thr Phe His Gln
65                  70                  75                  80

Trp Arg Asp Ala Arg Gln Val Tyr Gly Leu Asn Phe Ala Ser Lys Glu
                85                  90                  95

Glu Ala Thr Thr Phe Ser Asn Ala Met Leu Phe Ala Leu Asn Ile Met
                100                 105                 110

Asn Ser Gln Glu Gly Gly Pro Ser Thr Gln Arg Gln Val Gln Asn Gly
            115                 120                 125

Pro Ser Pro Glu Glu Met Asp Ile Gln Arg Arg Gln Val Met Glu Gln
        130                 135                 140

Gln His Arg Gln Glu Ser Leu Glu Arg Arg Ile Ser Ala Thr Gly Pro
145                 150                 155                 160
```

-continued

```
Ile Leu Pro Pro Gly His Pro Ser Ser Ala Ala Ser Thr Thr Leu Ser
            165                 170                 175

Cys Ser Gly Pro Pro Pro Pro Pro Pro Pro Val Pro Pro Pro Pro
            180             185                 190

Thr Gly Ser Thr Pro Pro Pro Pro Pro Leu Pro Ala Gly Gly Ala
        195                 200                 205

Gln Gly Thr Asn His Asp Glu Ser Ser Ala Ser Gly Leu Ala Ala Ala
        210                 215                 220

Leu Ala Gly Ala Lys Leu Arg Arg Val Gln Arg Pro Glu Asp Ala Ser
225                 230                 235                 240

Gly Gly Ser Ser Pro Ser Gly Thr Ser Lys Ser Asp Ala Asn Arg Ala
                245                 250                 255

Ser Ser Gly Gly Gly Gly Gly Leu Met Glu Glu Met Asn Lys Leu
            260                 265                 270

Leu Ala Lys Arg Arg Lys Ala Ala Ser Gln Thr Asp Lys Pro Ala Asp
            275                 280                 285

Arg Lys Glu Asp Glu Ser Gln Thr Glu Asp Pro Ser Thr Ser Pro Ser
    290                 295                 300

Pro Gly Thr Arg Ala Thr Ser Gln Pro Pro Asn Ser Ser Glu Ala Gly
305                 310                 315                 320

Arg Lys Pro Trp Glu Arg Ser Asn Ser Val Glu Lys Pro Val Ser Ser
                325                 330                 335

Leu Leu Ser Arg Val Lys Pro Ala Gly Ser Val Asn Asp Val Gly Leu
                340                 345                 350

Asp Ala Leu Asp Leu Asp Arg Met Lys Gln Glu Ile Leu Glu Glu Val
            355                 360                 365

Val Arg Glu Leu His Lys Val Lys Glu Glu Ile Ile Asp Ala Ile Arg
    370                 375                 380

Gln Glu Leu Ser Gly Ile Ser Thr Thr
385                 390
```

METHODS AND PRODUCTS FOR REGULATING CELL MOTILITY

RELATED APPLICATIONS

This application claims priority under 35 U.S.C. §119 to U.S. Provisional Patent Application No. 60/194,564, filed on Apr. 3, 2000, the entire contents of which is hereby incorporated by reference.

GOVERNMENT SUPPORT

The present invention was supported in part by a grant from the United States National Institutes of Health under contract/grant number GM58801. The U.S. Government may retain certain rights in the invention.

FIELD OF THE INVENTION

The invention relates to methods for regulating cell motility and related products. In particular methods for promoting and preventing cell migration are described herein.

BACKGROUND OF THE INVENTION

How a cell moves is one of the most compelling mysteries of cell biology. Cell migration forms the basis for higher order processes such as immune cell homing, wound healing, and axonal pathfinding. Migration depends on the coordinated execution and integration of complex individual processes. Although different cell types have unique approaches to cell movement, it is useful to consider animal cell migration in a generalized way. In its simplest form, movement requires that a cell generates and maintains a state of asymmetry or polarity.

Once polarized, a cell must execute a four-step cycle to migrate or translocate (reviewed in Lauffenburger, D. A., and Horwitz, A. F. (1996). Cell migration: a physically integrated molecular process. Cell 84, 359–69). First, a cell must extend a process, known as the leading edge, in the direction of movement. During this step, increased actin polymerization is seen in the area of the leading edge. This increased polymerization arises from the creation of new barbed ends that are oriented towards the membrane, either by nucleation of new filaments from pools of G-actin or by severing or uncapping of existing filaments. Actin monomers are added onto barbed ends until they are capped (Schafer, D. A., and Cooper, J. A. (1995). Control of actin assembly at filament ends. Annu Rev Cell Dev Biol 11, 497–518). The combination of actin nucleation and filament elongation is thought to play a critical role in the protrusion of the leading edge (Eddy, R. J., Han, J., and Condeelis, J. S. (1997). Capping protein terminates but does not initiate chemoattractant—induced actin assembly in Dictyostelium. J Cell Biol 139, 1243–53). Second, once a cell has extended a process, it must form semi-stable points of attachment with the underlying substratum to serve as anchor points. One class of attachment points, focal adhesions, contain aggregates of integrin receptors and a variety of cytosolic signaling and cytoskeletal proteins and serve as sites of bidirectional signaling between the extracellular matrix and the actin cytoskeleton (Schoenwaelder, S. M., and Burridge, K. (1999). Bidirectional signaling between the cytoskeleton and integrins. Curr Opin Cell Biol 11, 274–86). Although attachment of newly extended processes may be critical for cell translocation, process extension itself does not require adhesion (Bailly, M., Yan, L., Whitesides, G. M., Condeelis, J. S., and Segall, J. E. (1998). Regulation of protrusion shape and adhesion to the substratum during chemotactic responses of mammalian carcinoma cells. Exp Cell Res 241, 285–99). Third, once a cell has extended and anchored a new process, it must slide the cell body forward by traction. The fourth step is release of points of substratum attachment at the rear of the cell.

The evolutionarily-conserved Ena/VASP protein family has been implicated in the regulation of cell migration (Gertler, F. B., Niebuhr, K., Reinhard, M., Wehland, J., and Soriano, P. (1996). Mena, a relative of VASP and Drosophila Enabled, is implicated in the control of microfilament dynamics. Cell 87, 227–39). Enabled (Ena; SEQ ID NO: 9) was identified as a genetic suppressor of loss-of-function mutations in Drosophila Ableson tyrosine kinase (D-Abl) (Gertler, F. B., Doctor, J. S., and Hoffinann, F. M. (1990). Genetic suppression of mutations in the Drosophila abl proto-oncogene homolog. Science 248, 857–60). Loss-of-function mutations in Ena ameliorated the embryonic central nervous system defects associated with loss of D-Abl in combination with mutations in any of several known D-Abl modifier genes (Gertler, F. B., Corner, A. R., Juang, J L., Ahern, S. M., Clark, M. J., Liebl, E. C., and Hoffmann, F. M. (1995). enabled, a dosage-sensitive suppressor of mutations in the Drosophila Abl tyrosine kinase, encodes an Abl substrate with SH3 domain-binding properties. Genes Dev 9, 521–33). VASP was identified biochemically as an abundant substrate for cyclic-nucleotide dependent kinases in mammalian platelets (SEQ ID NO: 10); (Halbrugge, M., and Walter, U. (1990). Analysis, purification and properties of a 50,000-dalton membrane- associated phosphoprotein from human platelets. J Chromatogr 521, 335–43). Two other mammalian members of this protein family, Mena (mammalian Enabled; SEQ ID NO: 2 and EVL (Ena/VASP like; SEQ ID NO: 11), were identified by sequence similarity (Gertler, F. B., Niebuhr, K., Reinhard, M., Wehland, J., and Soriano, P. (1996). Mena, a relative of VASP and Drosophila Enabled, is implicated in the control of microfilament dynamics. Cell 87, 227–39).

All Ena/VASP family members share a conserved domain structure. The N-terminal third of the protein, the EVH1 (Ena VASP Homology) domain (Gertler, F. B., Niebuhr, K., Reinhard, M, Wehland, J, and Soriano, P. (1996). Mena, a relative of VASP and Drosophila Enabled, is implicated in the control of microfilament dynamics. Cell 87, 227–39), mediates subcellular targeting of Ena/VASP proteins to focal adhesions by binding to proteins containing a motif whose consensus is D/E FPPPPX D/E (SEQ ID NO: 1) (Niebuhr, K., Ebel, F., Frank, R., Reinhard, M., Domann, E., Carl, U. D., Walter, U., Gertler, F. B., Wehland, J., and Chakraborty, T. (1997). A novel proline-rich motif present in ActA of Listeria monocytogenes and cytoskeletal proteins is the ligand for the EVH1 domain, a protein module present in the Ena/VASP family. Embo J 16, 5433–44). Mutational analysis indicated that the phenylalanine residue, along with flanking acidic residues on either side, are critical for optimal binding (Carl, U. D., Pollmann, M., Orr, E., Gertler, F. B., Chakraborty, T., and Wehland, J. (1999). Aromatic and basic residues within the EVH1 domain of VASP specify its interaction with proline-rich ligands. Curr Biol 9, 715–8). The EVH1 ligand motif is found in a number of cellular proteins, including the focal adhesion proteins zyxin and vinculin. The central portion of Ena/VASP proteins contains proline-rich stretches, which have been reported to be binding sites for three types of proteins: the G-actin binding protein profilin, SH3 domain-containing proteins, and WW domain-containing proteins (Ermekova, K. S., Zambrano, N., Linn, H., Minopoli, G., Gertler, F., Russo, T., and Sudol, M. (1997). The WW domain of neural protein FE65 interacts with proline-rich motifs in Mena, the mammalian homolog of Drosophila enabled. *J Biol Chem* 272, 32869–77; Gertler, F. B., Niebuhr, K., Reinhard, M., Wehland, J., and Soriano, P. (1996). Mena, a relative of VASP and Drosophila Enabled, is implicated in the control of microfilament dynamics. *Cell* 87, 227–39). The C-terminal third of Ena/VASP proteins contains the EVH2 domain that binds in vitro to F-actin and has a putative coiled-coil region reported to be important for multimerization (Bachmann, C., Fischer, L., Walter, U., and Reinhard, M. (1999). The EVH2 domain of the vasodilator-stimulated phosphoprotein mediates tetramerization, F-actin binding, and actin bundle formation. *J Biol Chem* 274, 23549–57,; Huttelmaier, S., Harbeck, B., Steffens, O., Messerschmidt, T., Illenberger, S., and Jockusch, B. M. (1999). Characterization of the actin binding properties of the vasodilator-stimulatedphosphoprotein VASP. *FEBS Lett* 451, 68–74).

In addition to their capacity to bind profilin and actin, the localization of Ena/VASP proteins suggests that they may be involved in regulating actin dynamics and/or adhesion. In fibroblasts, Ena/VASP proteins are localized to focal adhesions, in a weak punctuate pattern along stress fibers and to the leading edge, while in neuronal growth cones, they are concentrated at the distal tips of filopodia (Reinhard, M., Halbrugge, M., Scheer, U., Wiegand, C., Jockusch, B. M., and Walter, U. (1992). The 46/50 kDa phosphoprotein VASP purifiedfrom human platelets is a novel protein associated with actin filaments and focal contacts. *Embo J.* 11, 2063–70; Gertler, F. B., Niebuhr, K., Reinhard, M., Wehland, J., and Soriano, P. (1996). Mena, a relative of VASP and Drosophila Enabled, is implicated in the control of microfilament dynamics. *Cell* 87, 227–39; Lanier, L. M., Gates, M. A., Witke, W., Menzies, A. S., Wehman, A. M, Macklis, J. D., Kwiatkowski, D., Soriano, P., and Gertler, F. B. (1999). Mena is required for neurulation and commissure formation. *Neuron* 22, 313–25). Genetic analyses of Ena/VASP family members in flies and mice demonstrated that these proteins function in processes that involve cell shape change, and movement including platelet aggregation and axon guidance (Aszodi, A., Pfeifer, A., Ahmad, M., Glauner, M., Zhou, X. H., Ny, L., Andersson, K. E., Kehrel, B., Offermanns, S., and Fassler, R. (1999). The vasodilator-stimulated phosphoprotein (VASP) is involved in cGMP- and cAMP-mediated inhibition of agonist-induced platelet aggregation, but is dispensable for smooth muscle function. Embo J. 18, 37–48; Wills, Z., Bateman, J., Korey, C. A., Corner, A., and Van Vactor, D. (1999). The tyrosine kinase Abl and its substrate enabled collaborate with the receptor phosphatase Dlar to control motor axon guidance. *Neuron* 22, 301–12). In mice, a dosage-sensitive genetic interaction between Mena and profilin I supports a model in which these two proteins function in concert during development (Lanier, L. M., Gates, M. A., Witke, W., Menzies, A. S., Wehman, A. M., Macklis, J. D., Kwiatkowski, D., Soriano, P., and Gertler, F. B. (1999). Mena is required for neurulation and commissure formation. *Neuron* 22, 313–25).

Ena/VASP proteins are also implicated in actin dynamics by their role in facilitating the actin-based motility of the intracellular bacterial pathogen Listeria monocytogenes. The Listeria protein, ActA is required for the formation of actin tails characteristic of motile bacteria (Kocks, C., Gouin, E., Tabouret, M., Berche, P., Ohayon, H., and Cossart, P. (1992). L. monocytogenes-induced actin assembly requires the actA gene product, a surface protein. *Cell* 68, 521–31; Domann, E., Wehland, J., Rohde, M., Pistor, S., Hartl, M., Goebel, W., Leimeister-Wachter, M., Wuenscher, M., and Chakraborty, T (1992). A novel bacterial virulence gene in Listeria monocytogenes required for host cell microfilament interaction with homology to the proline-rich region of vinculin. *Embo J* 11, 1981–90). Furthermore, the motility of the intracellular pathogen Listeria monocytogenes resulting from rapid actin polymerization at one pole of the bacterium requires Ena (Laurent, V., Loisel, T. P., Harbeck, B., Wehman, A., Grobe, L., Jockusch, B. M., Wehland, J., Gertler, F. B., and Carlier, M. F. (1999). Role of proteins of the Ena/VASP family in actin-based motility of Listeria monocytogenes. *J. Cell Biol* 144, 1245–58; Loisel, T. P., Boujemaa, R., Pantaloni, D., and Carlier, M. F. ( 999). Reconstitution of actin-based motility of Listeria and Shigella using pure proteins. *Nature* 401, 613–6).

ActA is a multi-domain protein on the surface of the bacteria that interacts with host cell factors to trigger actin assembly (Pistor, S., Chakraborty, T., Walter, U., and Wehland, J. (1995). The bacterial actin nucleator protein ActA of Listeria monocytogenes contains multiple binding sites for host microfilament proteins. *Curr Biol* 5, 517–25). Actin nucleation is driven by ActA-mediated activation of the Arp2/3 complex (Welch, M. D., Rosenblatt, J., Skoble, J., Portnoy, D. A., and Mitchison, T. J. (1998). Interaction of human Arp2/3 complex and the Listeria monocytogenes ActA protein in actinfilament nucleation. *Science* 281, 105–8). Ena/VASP proteins are the only host cell factors known to bind directly to ActA in vivo, which contains four optimized copies of the D/E FPPPPXDDE (SEQ ID NO: 1) EVH1 ligand motif (Niebuhr, K., Ebel, F., Frank, R., Reinhard, M., Domann, E., Carl, U. D., Walter, U., Gertler, F. B., Wehland, J., and Chakraborty, T. (1997). *A novel proline-rich motif present in ActA of Listeria monocytogenes and cytoskeletal proteins is the ligand for the EVH1 domain, a protein module present in the Ena/VASP family. Embo J.* 16, 5433–44). Mutation of these repeats leads to a defect in bacterial movement, despite the fact that an actin cloud and short actin tails still form around the bacterium (Smith, G. A., Theriot, J. A. and Portnoy, D. A., 1996. The tandem repeat domain in the Listeria monocytogenes ActA protein controls the rate of actin-based motility, the percentage of moving bacteria, and the localization of vasodilator-stimulatedphosphoprotein and profilin. *J. Cell Bio.* 135:647–660; Niebuhr, K., Ebel, F., Frank, R., Reinhard, M., Domann, E., Carl, U. D., Walter, U., Gertler, F. B., Wehland, J., and Chakraborty, T. (1997). A novelproline-rich motif-present in ActA of Listeria monocytogenes and cytoskeletal proteins is the ligand for the EVH1 domain, a protein module present in the EnalVASP family. *Embo J* 16, 5433–44). In vitro experiments using either depleted cell-free extracts or reconstitution with purified proteins directly demonstrated that Ena/VASP are required for efficient actin tail formation and normal bacterial motility (Laurent, V., Loisel, T. P., Harbeck, B., Wehman, A., Grobe, L., Jockusch, B. M., Wehland, J., Gertler, F. B., and Carlier, M. F. (1999). Role of proteins of the Ena/VASP family in actin-based motility of Listeria monocytogenes. *J Cell Biol* 144, 1245–58; Loisel, T. P., Boujemaa, R., Pantaloni, D., and Carlier, M. F. (1999). Reconstitution of actin-based motility ofListeria and Shigella using pure proteins. *Nature* 401, 613–6). It has been proposed that Ena/VASP proteins act to increase the rate of actin filament extension by increasing the local pool of profilin-actin complexes (Beckerle, M. C. (1998). Spatial control of actinfilament assembly: lessons from Listeria. *Cell* 95, 741–8). Listeria has been proposed as a model for the reorganization of actin at the leading edge of a motile cell. Recent work using GFP-tagged VASP demonstrated a strong correlation between membrane extension rates and the concentration of VASP at the leading edge (Rottner, K., Behrendt, B., Small, J. V., and Wehland, J. (1999). VASP dynamics during lamellipodia protrusion. *Nat Cell Biol* 1, 321–2). Based on localization studies and the Listeria experiments, it has been proposed that Ena/VASP proteins serve to promote actin-based cell movement.

U.S. Pat. No. 5,990,087 issued to Lal et al., describes a human Ena/VASP—like protein splice variant referred to as EVL1 and methods of use thereof. The patent teaches that EVL1 has an activity which is similar to the activity that has been proposed for the known Ena/VASP proteins. Specifically, the patent teaches that EVL1 antagonists which reduce EVL1 activity within a cell can be used to treat or prevent cancer and EVL1 agonists which increase EVL1 activity within a cell can be used to treat or prevent a nervous system disorder.

SUMMARY OF THE INVENTION

The invention relates, in some aspects, to methods for promoting or preventing cellular migration and for various therapeutic treatments using Ena/VASP inhibitors and activators. It has been discovered, surprisingly, that Ena/VASP proteins are negative regulators of cell motility. Because of the role of Ena/VASP proteins in the positive regulation of cell motility in the Listeria system and because of the localization of Ena/VASP in focal adhesions and neuronal growth cones it was widely believed in the prior art that Ena/VASP proteins are universally positive regulators of cell motility. The prior art such as U.S. Pat. No. 5,990,087 hypothesized that Ena/VASP proteins play a positive role in regulating cell motility and thus inhibition of these proteins should be beneficial for the treatment of cancer by reducing or eliminating cellular migration and thus metastasis. In contrast to the teachings of the prior art, it was discovered that Ena/VASP proteins are actually negative regulators of cell motility. When Ena/VASP protein activity is upregulated cell motility is reduced significantly. Alternatively when Ena/VASP protein activity is downregulated cell motility is enhanced significantly. Thus, it has been discovered according to the invention that upregulation of Ena/VASP protein activity can be used to slow cellular migration and thus to prevent cell metastasis and that downregulation of Ena/VASP protein activity can be used to increase cell motility to promote would healing and tissue regeneration.

In one aspect the invention is a method for preventing mammalian cell migration. The method involves inducing a functional Ena/VASP protein in a mammalian cell in an effective amount for preventing cell migration. In other aspects the invention is a method for preventing tumor cell metastasis in a subject. The method involves administering to a subject having or at risk of developing a metastatic cancer a plasma membrane targeting compound in an effective amount for preventing cell migration in order to prevent tumor cell metastasis. In yet other aspects, the invention is a method for preventing or treating inflammatory disease in a subject. The method involves administering to a subject having or at risk of developing an inflammatory disease a plasma membrane targeting compound in an effective amount for preventing cell migration in order to prevent or treat the inflammatory disease.

In some preferred embodiments the functional Ena/VASP protein is induced by contacting the mammalian cell with an Ena/VASP activator. The Ena/VASP activator can be a plasma membrane targeting compound that targets the endogenous Ena/VASP protein to the plasma membrane or in other embodiments it can be exogenous EDa/VASP protein. The plasma membrane targeting compound may be an Ena/VASP binding molecule conjugated to a plasma membrane targeting domain. Optionally the Ena/VASP binding molecule is an EVH1 binding molecule. EVH1 binding molecules include but are not limited to FPPPP peptides (SEQ ID NO.: 3) and peptide mimetics. In other embodiments the functional Ena/VASP protein is induced by expression of exogenous Ena/VASP protein in the cell.

The mammalian cell may be any type of cell but in some embodiments is a tumor cell. The tumor cell may be a tumor cell that is treated in vitro or in vivo.

The Ena/VASP protein may be any type of Ena/VASP protein known in the art, including proteins having homology to known Ena/VASP proteins. In some embodiments the Ena/VASP protein is a protein selected from the group consisting of Mena, VASP and Evl.

The invention in another aspect involves a method for promoting cell migration. The method is performed by depleting a mammalian cell of a functional Ena/VASP protein to promote cell migration. In some embodiments the functional Ena/VASP protein is depleted by contacting the mammalian cell with an Ena/VASP inhibitor.

In another related aspect the invention is a method for promoting wound healing. The method involves contacting a mammalian cell involved in wound healing with an Ena/VASP inhibitor to promote migration of the mammalian cell to the site of the wound. In some embodiments the Ena/VASP inhibitor is administered in vivo to a subject at the site of the wound.

The invention in other aspects relates to a method for promoting tissue generation. The method involves contacting mammalian cells of a tissue type with an Ena/VASP inhibitor to promote actin polymerization and tissue formation on a scaffold. In some embodiments the scaffold is an artificial scaffold in vitro and optionally the scaffold is implanted in vivo once the tissue has generated. In other embodiments the scaffold is an artificial scaffold in vivo. Optionally the scaffold is a naturally occurring tissue scaffold in vivo. In other embodiments the Ena/VASP inhibitor is administered to a site of damaged nerve cells in a subject on a naturally occurring tissue scaffold.

In some preferred embodiments the Ena/VASP inhibitor is an Ena/VASP binding molecule conjugated to an intracellular targeting domain that targets Ena/VASP protein to a surface remote from the plasma membrane. The Ena/VASP binding molecule preferably is an EVH1 binding molecule, which may optionally be a FPPPP peptide (SEQ ID NO.: 3) or a peptide mimetic. In other embodiments the Ena/VASP inhibitor is an Ena/VASP antisense molecule.

The mammalian cell may be any type of cell. In some preferred embodiments the mammalian cell is a fibroblast, a nerve cell, a glial cell, an epithelial cell, an endothelial cell and a muscle cell. In some embodiments the cell is a fibroblast and the fibroblast is contacted with the Ena/VASP inhibitor in vitro and in other embodiments the fibroblast is applied to the site of a wound in vivo.

The Ena/VASP protein may be any type of Ena/VASP protein known in the art, including proteins having homology to known EnaNASP proteins. In some embodiments the Ena/VASP protein is a protein selected from the group consisting of Mena, VASP and Evl.

According to other aspects of the invention a method for promoting tissue regeneration. In some embodiments this method is useful for preventing or treating neurodegenerative diseases. The method involves administering to a subject having or at risk of neurodegeneration an Ena/VASP inhibitor in an amount effective to promote tissue regeneration or to prevent neurodegeneration.

In some embodiments the Ena/VASP inhibitor is administered locally to the site of tissue where generation is desired or to the site of neurodegeneration. In other embodiments the Ena/VASP inhibitor is administered to a nerve cell in vitro and the nerve cell is delivered to the subject at the site of neurodegeneration. In yet other embodiments the Ena/VASP inhibitor is administered in a sustained release vehicle at the site of neurodegeneration.

Preferably the subject having or at risk of neurodegeneration has or is at risk of developing Alzheimer's disease, Down Syndrome; Parkinson's disease; amyotrophic lateral sclerosis (ALS), stroke, direct trauma, Huntington's disease, epilepsy, ALS-Parkinsonism-dementia complex; progressive supranuclear palsy; progressive bulbar palsy, spinomuscular atrophy, cerebral amyloidosis, Pick's atrophy, Retts syndrome; Wilson's disease, Striatonigral degeneration, corticobasal ganglionic degeneration; dentatorubral atrophy, olivo-pontocerebellar atrophy, paraneoplastic cerebellar degeneration; Tourettes syndrome, hypoglycemia; hypoxia; Creutzfeldt-Jakob disease; or Korsakoff s syndrome.

In one embodiment the Ena/VASP inhibitor is administered in an effective amount for preventing EnalVASP proteins from interacting with FE65, profilinl or profilin2.

The invention also relates to methods of enhancing or disrupting learning and memory. It was discovered according to the invention that inhibition of Ena/VASP proteins is sufficient to enhance learning and memory and also that activation of Ena/VASP proteins is sufficient to disrupt learning and memory. Thus in one aspect the invention relates to a method for enhancing learning and memory by administering to a subject an Ena/VASP inhibitor in an amount effective to enhance learning and memory. In some embodiments the subject has or is at risk of developing a learning disorder selected from the group consisting of Alzheimer's disease, Creutzfeld-Jakob disease, brain damage, senile dementia, Korsakow's disorder, and age-related memory loss. In other embodiments the Ena/VASP inhibitor is administered in an effective amount for inhibiting the activity of Mena in a synapse of the subject. In another aspect the invention relates to a method for disrupting learning and memory by administering to a subject an Ena/VASP activator in an amount effective to disrupt learning and memory.

The inhibitor or activator can be administered systemically or locally and in some embodiments is specifically targeted to the brain.

The invention also encompasses compositions and kits. In one aspect the invention is a composition of an Ena/VASP inhibitor in an effective amount for promoting cellular migration and a pharmaceutically acceptable carrier and in other aspects the invention is a composition of an effective amount for preventing cellular migration, of an Ena/VASP activator in a pharmaceutically acceptable carrier.

According to other aspects of the invention methods for identifying a therapeutic Ena/VASP activator or inhibitor are provided. The method involves contacting a mammalian cell with a putative Ena/VASP activator or inhibitor and either determining the effect of the putative Ena/VASP activator or inhibitor on cell migration or determining the intracellular location of endogenous Ena/VASP. The Ena/VASP activator or inhibitor is identified by observing either a decreased rate of migration or an increased rate of migration with respect to an untreated control mammalian cell respectively or altered localization.

The putative Ena/VASP activator or inhibitor may be obtained from any source but in preferred embodiments it is obtained from a peptide library of compounds, a small molecule library of compounds, or a peptidomimetic library of compounds. In other embodiments the putative Ena/VASP activator or inhibitor is obtained from a mixture of compounds identified using an anti-idiotypic antibody.

The invention also includes modified cells and screening assays based on those cells. Thus in one aspect the invention is a modified cell which is an Ena/VASP double negative cell. Preferably the cell is a fibroblast and preferably the cell is a Mena/VASP double mutant. In one embodiment the cell is a mammalian cell. The cell may be used in a method for identifying a therapeutic compound for inhibiting cellular migration. The method involves contacting the modified cell with a putative compound for inhibiting cellular migration, and determining the effect of the putative compound on cellular migration, wherein a putative compound which inhibits cellular migration is a therapeutic compound.

In yet other aspects the invention relates to a compound having an actin binding domain and a cell motility domain, but which does not include a Listeria motility domain. In one embodiment the actin binding domain is a peptide sequence corresponding to amino acids 411–429 of Mena or a conservative substitution thereof. In another embodiment the cell motility domain includes a conserved EVH1 domain. In preferred embodiments the cell motility domain is a peptide sequence corresponding to amino acids 1–280 of Mena or a conservative substitution thereof. The compound may be a peptide having a sequence corresponding to a conservative substitution thereof. In yet other embodiments the compound is a mimetic.

A modified Ena/VASP protein is also provided according to aspects of the invention. The modified Ena/VASP protein includes the amino acid sequence of the mature peptide of SEQ ID NO: 2 wherein at least one amino acid residue has been substituted and wherein the substitution is selected from the group consisting of (a) a non-conservative or conservative substitution of a serine residue corresponding to position 236 or 376 of SEQ ID NO: 2; (b) a non-conservative substitution or deletion of one or more residues corresponding to position 411–429 of SEQ ID NO: 2; (c) a conservative substitution of at least one residue corresponding to position 281–344 of SEQ ID NO: 2; (d) a non-conservative substitution or deletion of at least one residue corresponding to position 281–344 of SEQ ID NO: 2; and (e) a non-conservative or conservative substitution or deletion of one or more residues corresponding to position 411–429 of SEQ ID NO: 2.

The invention in another aspect is a method for identifying a therapeutic compound for inhibiting or promoting cellular migration. The method involves screening one or more putative compounds for the ability to interact with an actin barbed end to identify an actin binding molecule, and determining the effect of the actin binding molecule on cellular migration to determine whether the actin binding molecule is a therapeutic compound for inhibiting or promoting cellular migration. In one embodiment a composition identified by the method is included in the invention.

Each of the embodiments of the invention can encompass various recitations made herein. It is, therefore, anticipated that each of the recitations of the invention involving any one element or combinations of elements can, optionally, be included in each aspect of the invention.

BRIEF DESCRIPTION OF THE DRAWINGS

FIG. 2 depicts a schematic diagram of mito targeting constructs. DEPPPP is SEQ ID NO.:12. DAPPPP is SEQ ID NO.: 13.

BRIEF DESCRIPTION OF THE SEQUENCES

Figure 1:
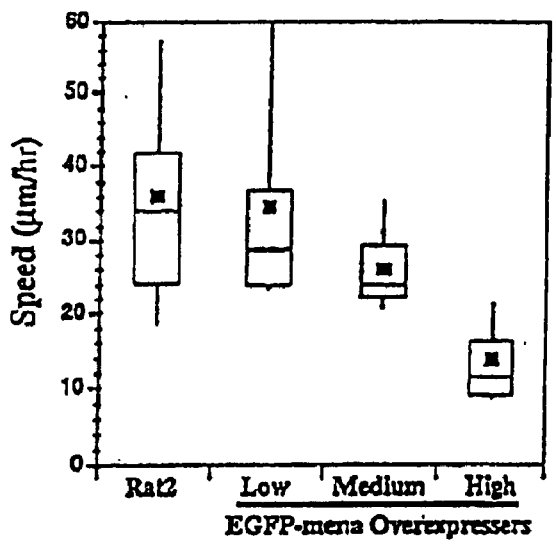
FIG. 1: Overexpression of EGFP-Mena inhibits cell motility in a dose responsive manner. Box and whisker plots of speed. Dot indicates mean, middle line of box indicates median, top of box indicates 75th quatrile, bottom of box indicates 25th quatrile and 'whiskers' indicate extent of 10th and 90th percentiles respectively. Data comes from ≧20 cells per treatment from 2–3 separate experiments and was analyzed by one-way ANOVA. p-value was <0.0001 and treatments with non-overlapping 95% confidence intervals are marked by an asterisk.

SEQ. ID. NO. 1 is the protein consensus motif D/E FPPPPXDDE.

SEQ. ID. NO. 2 is the Mena protein sequence.

SEQ. ID. NO. 3 is the protein consensus motif FPPPP.

SEQ. ID. NO. 4 is the control protein consensus motif APPPP.

SEQ. ID. NO. 5 is AdA.

SEQ. ID. NO. 6 is CAAX.

SEQ. ID. NO. 7 is the protein consensus motif FPPPP-CAAX.

SEQ. ID. NO. 8 is the control protein consensus motif APPPP-CAAX.

SEQ. ID. NO. 9 is Enabled (Ena) protein sequence.

SEQ. ID. NO. 10 is VASP protein sequence.

SEQ. ID. NO. 11 is EVL (Ena/VASP like) protein sequence.

SEQ. ID. NO. 12 is the protein consensus motif DFPPPP.

SEQ. ID. NO. 13 is the protein consensus motif DAPPPP.

SEQ. ID. NO. 14 is the protein consensus motif D/EFPPPP.

DETAILED DESCRIPTION

The invention is based in part on the surprising discovery that Ena/VASP proteins are negative regulators of cell motility. It was generally believed in the prior art that Ena/VASP proteins were positive regulators of cell motility. Thus, the finding that Ena/VASP proteins negatively regulate cell motility was quite surprising and led to the identification of several new therapeutic strategies, which are described and claimed herein.

The discovery that mammalian cell migration can be prevented by inducing functional Ena/VASP protein in the cell has important implications for cancer cell metastasis, immune regulation, and inflammatory disease.

The invention is useful for treating and/or preventing tumor cell metastasis in a subject. The terms "prevent" and "preventing" as used herein refer to inhibiting completely or partially the biological effect, e.g., metastasis of a cancer or tumor cell, as well as inhibiting any increase in the biological effect, e.g., metastasis of a cancer or tumor cell.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

A "subject at risk of having a cancer" as used herein is a subject who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated to induce Ena/VASP protein activity the subject may be able to prevent any cancer that does form from becoming metastatic.

In some aspects of the invention the Ena/VASP activity is induced in an effective amount to prevent migration of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., *Cell* 64:327–336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

Preferably the tumor cells are prevented from crossing a barrier. The barrier for the tumor cells may be an artificial barrier in vitro or a natural barrier in vivo. In vitro barriers include but are not limited to extracellular matrix coated membranes, such as Matrigel. Thus the Ena/VASP proteins can be induced in cells which can then be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," *Int. J. Cancer* (1992) 52:378–383. Matrigel is a reconstituted basement membrane containing type IV collagen, laminin, heparan sulfate proteoglycans such as perlecan, which bind to and localize bFGF, vitronectin as well as transforming growth factor-$\beta$ (TGF-$\beta$), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

The invention is also useful for treating and/or preventing disorders associated with inflammation in a subject. When Ena/VASP protein activity is induced in immune or hematopoetic cells the ability of the cells to migrate is reduced. Thus induction of Ena/VASP activity in immune cells is useful for preventing inflammation associated with immune cell migration and for treating and preventing inflammatory disorders and ischemic diseases.

Inflammatory disorders and ischemic diseases are characterized by inflammation associated with neutrophil migration to local tissue regions that have been damaged or have otherwise induced neutrophil migration and activation. While not intending to be bound by any particular theory, it is believed that excessive accumulation of neutrophils resulting from neutrophil migration to the site of injury, causes the release toxic factors that damage surrounding tissue. When the inflammatory disease is an acute stroke a tissue which is often damaged by neutrophil stimulation is the brain. As the active neutrophils accumulate in the brain an infarct develops.

An "inflammatory disease or condition" as used herein refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil accumulation at a local tissue site. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

An "ischemic disease or condition" as used herein refers to a condition characterized by local inflammation resulting from an interruption in the blood supply to a tissue due to a blockage or hemorrhage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The methods of the invention are well suited for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption in blood flow to the brain resulting from either a thromboembolism or hemorrhage. A stroke causes a loss of neurons typically resulting in a neurologic deficit that may improve but that does not entirely resolve. Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms. The term thromboembolism is used to describe thrombotic and embolic strokes. Hemorrhagic stroke is caused by the rupture of a blood vessel in a subarachnoid space or intracerebral tissue.

A preferred method of the invention involves the in vivo treatment of thromboembolic stroke by inducing Ena/VASP protein activation in a cell of a subject experiencing or at risk of developing an acute thromboembolic stroke in an amount effective to reduce brain injury which would otherwise occur as a result of neutrophil accumulation caused by the stroke.

The Ena/VASP protein activation may be induced in a cell of a subject to treat or prevent cancer metastasis or inflammatory disorders alone or in combination with the administration of other therapeutic compounds for the treatment or prevention of these disorders.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma- I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202–1263, of Goodman and Gilman's "The Pharmacological Basis of Therapeutics", Eighth Edition, 1990, McGraw-Hill, Inc. (Health Professions Division).

Anti-inflammatory drugs include but are notlimited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Ena/VASP may be induced in a cell using an Ena/VASP activator or by inducing expression of exogenous Ena/VASP protein within the cell. An "Ena/VASP activator" as used herein refers to any compound that induces activation of an endogenous Ena/VASP protein. An Ena/VASP activator includes but is not limited to compounds which activate endogenous Ena/VASP proteins and Ena/VASP nucleic acids. A particularly preferred compound that activates endogenous Ena/VASP protein is a plasma membrane targeting compound that includes an Ena/VASP binding molecule conjugated to a plasma membrane targeting domain. Examples of this type of molecule are described in more detail in the Examples section. An "Ena/VASP binding molecule" as used herein is any type of molecule that specifically binds to Ena/VASP. Ena/VASP proteins are known to bind to EVH1 binding domains, such as the FPPPP (SEQ ID NO. 3) domain. Other types of Ena/VASP binding molecules include antibodies, antibody fragments, other peptides, mimetics, etc. Ena/VASP binding molecules can be identified using routine binding assays.

A "Plasma membrane targeting compound " as used herein refers to any molecule or compound which is specific for a plasma membrane of a particular cell and which can be used to direct the Ena/VASP protein or nucleic acid to the plasma membrane. For instance the plasma membrane targeting compound may be an amino acid sequence which extends across the membrane; a lipid membrane retention compound which associates with the lipids of the cell surface membrane, or a non-peptide targeting compound which associates with the proteins or lipids. The lipid membrane retention compounds generally have a lipid of from about 12 to 24 carbon atoms, particularly 14 carbon atoms, more particularly myristoyl, joined to a signal sequence such as glycine, lysine, or arginine (Kaplan, et al., *Mol. Cell. BioL* (1988) 8, 2435). Other compounds are described in Carr, et al., *PNAS USA* (1988) 79, 6128; Aitken, et al., *FEBS Lett.* (1982) 150, 314; Henderson, et al., *PNAS USA* (1983) 80, 319; Schulz, et al., *Virology* (1984), 123, 2131; Dellman, et al., *Nature* (1985) 314, 374, and reviewed in *Ann. Rev. of Biochem.* (1988) 57,69; Gill, *Structure*, 3:1285–1289 (1995); Newton, *Current Biology*, 5:973–976 (1995)). Generally, amino acid compounds have from about 18–30 amino acids, more usually about 20–30 amino acids with a primarily neutral, non-polar amino acid central portion, and polar amino acids, frequently charged amino acids at the termini. Generally these molecules have about 1–2 charged, primarily basic amino acids at the termini followed by a helical break residue, e.g. pro- or gly-. Plasma membrane targeting compounds include but are not limited to LIM, myristoyl signal sequence ,C2, pleckstrin homology domains and other amino acid and lipid membrane retention compounds.

The invention, therefore, embraces peptide and non-peptide binding agents which, for example, can be antibodies or fragments of antibodies having the ability to selectively bind to Ena/VASP proteins. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York,; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized " antibodies in which non-human CDRs are covalently joined to human FR and/or Fc/pFc' regions to produce a functional antibody. See, e.g., U.S. Pat. No. 4,816,567, 5,225,539, 5,585,089, 5,693,762 and 5,859, 205.

Thus, for example, PCT International Publication Number WO92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric " antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to Ena/VASP proteins. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention, including human antibodies. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the Ena/VASP protein. This process can be repeated through several cycles of reselection of phage that bind to the Ena/VASP protein. Repeated rounds lead to enrichment of phage bearing particular sequences. DNA sequence analysis can be conducted to identify the sequences of the expressed polypeptides. The minimal linear portion of the sequence that binds to the Ena/VASP protein can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the Ena/VASP proteins. Thus, the Ena/VASP proteins of the invention, or a fragment thereof, can be used to screen peptide libraries, including phage display libraries, to identify and select peptide binding partners of the Ena/VASP proteins of the invention. Such molecules can be used, as described, for targeting endogenous Ena/VASP proteins, but can also be used in screening assays, for purification protocols, for interfering directly with the functioning of Ena/VASP protein and for other purposes that will be apparent to those of ordinary skill in the art.

The crystal structure of Ena/VASP proteins has been elucidated and extensively described in the prior art. The types of structures which bind to Ena/VASP proteins is also known. For instance it is known that the EVH1 domain of Ena/VASP proteins bind to peptides having the motif FPPPP (SEQ ID NO.: 3), and that the central portion of Ena/VASP proteins bind to at least three types of proteins, G-actin binding protein profilin, SH3 domains and WW domains. The WW domain, for instance, is a small functional domain found in a large number of proteins from a variety of species including humans, nematodes, and yeast. Its name is derived from the observation that two tryptophan residues, one in the amino terminal portion of the WW domain and one in the carboxyl terminal portion, are almost invariably conserved. WW domains are about 30 to 40 amino acids in length and thus are quite small for a functional domain. In general WW domains are flanked by stretches of amino acids rich in histidine or cysteine which may be metal-binding sites. The center of the WW domains is hydrophobic, but a high number of charged residues are also present throughout the motif, which are characteristic features of functional domains involved in protein—protein interactions (Bork and Sudol, 1994, *Trends in Biochem. Sci.* 19.531–533). Among other proteins having WW domains, the rat transcription factor FE65 possesses an amino terminal activation region that includes a WW domain (Bork and Sudol, 1994, *Trends in Biochem. Sci.* 19:531–533). Src homology 3 (SH3) domains are another class of compounds that bind to Ena/VASP proteins. SH3 domains have been described extensively in the prior art. See e.g., Pawson, 1995 *Nature* 373:573–580; Cohen, 1995, *Cell* 80:237–248 and Koch et al., 1991, *Science* 252:668–674.

Based on this information peptide and non-peptide libraries which are based on the known Ena/VASP binding proteins can easily be generated by those of skill in the art. Commercial entities such as ArQule (Woburn, Mass.) prepare custom libraries for the generation of mimetic compounds. The Ena/VASP binding compounds or putative binding compounds in such libraries may be identified using any of the screening assays or methods described below or in the Examples.

In addition to activation of endogenous Ena/VASP, exogenous Ena/VASP proteins can be expressed in mammalian cells, either by delivery of exogenous proteins or by delivery of exogenous nucleic acids encoding for an Ena/VASP protein which can be expressed within the cell. When exogenous Ena/VASP is added, preferably it includes a plasma membrane targeting sequence. Preferably exogenous nucleic acids encoding an Ena/VASP protein are delivered to the cell within an expression vector in order to produce functional Ena/VASP proteins within the cells. The exogenous Ena/VASP proteins useful according to the invention include but are not limited to Mena, VASP, Ev1, and Evl1. The nucleic acid and protein sequences for each of these molecules is attached hereto as SEQ ID Nos 2 and 9–11. The protein sequences for some Mena mutants are described in the examples.

The exogenous nucleic acids useful according to the invention are isolated. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulatable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulatable by standard techniques known to those of ordinary skill in the art. An isolated nucleic acid as used herein is not a naturally occurring chromosome.

The exogenous Ena/VASP nucleic acids useful for delivery to the cell include nucleic acid sequences coding for Ena/VASP proteins operably joined to expression sequences, optionally in a vector. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding an Ena/VASP protein or fragment or variant thereof. That heterologous DNA (RNA) is placed under operable control of transcriptional elements to permit the expression of the heterologous DNA in the host cell.

Preferred systems for mRNA expression in mammalian cells are those such as pcDNA3.1 and pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein-Barr Virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant for the expression of an antigen is disclosed by Warnier et al., in intradermal injection in mice for immunization against P1A (*Int. J. Cancer,* 67:303–310, 1996). Additional vectors for delivery of nucleic acid are provided below.

The Ena/VASP nucleic acids useful for expression in cells include the sequences provided in the sequence listing as well as functional homologs, alleles, and variants thereof. As detailed herein, the foregoing Ena/VASP binding molecules may be used for example for therapeutic as well as diagnostic purposes, e.g., to identify cells expressing the protein or the intracellular location of the protein to purify protein. The Ena/VASP binding compounds also may be coupled to specific diagnostic labeling agents for imaging of cells and tissues that express Ena/VASP proteins or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. Other diagnostic agents useful in the invention will be apparent to one of ordinary skill in the art.

Homologs and alleles of the Ena/VASP nucleic acids useful according to the invention can be identified by conventional techniques. Thus, the invention encompasses the use of nucleic acid sequences which code for Ena/VASP proteins, i.e., disclosed in the sequence listing, as well as, homologs and alleles thereof, as well as other molecules which hybridize under stringent conditions to the nucleic acids disclosed in the sequence listing.

The term "stringent hybridization conditions " and the like as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, stringent hybridization conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15 M. sodium chloride/0.15 M. sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1–0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of Ena/VASP nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity and/or at least 90% amino acid identity to the sequences of Ena/VASP nucleic acid and polypeptides, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://www.ncbi.nlm.nih.gov, using default settings. Pairwise and ClustalW alignments (BLOSUM30 matrix setting) as well as Kyte-Doolittle hydropathic analysis can be obtained using the MacVector sequence analysis software (Oxford Molecular Group).

Watson-Crick complements of the foregoing nucleic acids also are embraced by the invention.

In screening for Ena/VASP genes, a Southern blot may be performed using the foregoing conditions, together with a radioactive probe. In screening for the expression of Ena/VASP nucleic acids, Northern blot hybridizations using the foregoing conditions can be performed on the cells in which the exogenous Ena/VASP is being expressed. Amplification protocols such as polymerase chain reaction using primers which hybridize to the sequences presented also can be used for detection of the Ena/VASP genes or expression thereof.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Ena/VASP protein. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. Nucleic acids useful according to the invention also include modified nucleic acid molecules which include additions, substitutions and deletions of one or more nucleotides but which have the same biological function as Ena/VASP proteins.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The exogenous Ena/VASP of the invention also provides isolated polypeptides (including whole proteins and partial proteins) encoded by the foregoing Ena/VASP nucleic acids which can be delivered directly to the cells, or functional variants or fragments thereof. As used herein with respect to exogenous polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins. As used herein, a "variant" of an Ena/VASP protein is a polypeptide which contains one or more modifications to the primary amino acid sequence of an Ena/VASP protein.

Modifications to an Ena/VASP protein are typically made to the nucleic acid which encodes the Ena/VASP protein, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the Ena/VASP amino acid sequence. One of skill in the art will be familiar with methods for predicting the effect on protein conformation of a change in protein sequence, and can thus "design" a variant Ena/NASP protein according to known methods. One example of such a method is described by Dahiyat and Mayo in *Science* 278:82–87, 1997, whereby proteins can be designed de novo. Another is described in the Examples section. The method can be applied to a known protein to vary a only a portion of the polypeptide sequence. By applying the computational methods of Dahiyat and Mayo, specific variants of an Ena/VASP protein can be proposed and tested to determine whether the variant retains a desired conformation. Specific examples of mutants are disclosed in FIG. 9.

In general, variants include Ena/VASP proteins which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of an Ena/VASP protein by eliminating proteolysis by proteases in an expression system (e.g., dibasic amino acid residues in yeast expression systems in which KEX2 protease activity is present).

Mutations of a nucleic acid which encode an Ena/VASP protein preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant Ena/VASP proteins) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of an Ena/VASP gene or cDNA clone to enhance expression of the polypeptide. The activity of variants of Ena/VASP proteins can be tested by cloning the gene encoding the variant Ena/VASP protein into a bacterial or mammalian expression vector, introducing the vector into an appropriate host cell, expressing the variant Ena/VASP protein, and testing for a functional capability of the Ena/VASP proteins as disclosed herein. For example, the variant Ena/VASP protein can be tested for its effect on cell motility as disclosed in the Examples.

The skilled artisan will also realize that conservative amino acid substitutions may be made in Ena/VASP proteins to provide functionally equivalent variants of the foregoing polypeptides, i.e., the variants retain the functional capabilities of the Ena/VASP proteins. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants of the Ena/VASP proteins include conservative amino acid substitutions of the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of Ena/VASP proteins to produce functionally equivalent variants of Ena/VASP proteins typically are made by alteration of a nucleic acid encoding an Ena/VASP protein. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding an Ena/VASP protein. The activity of functionally equivalent fragments of Ena/VASP proteins can be tested by cloning the gene encoding the altered Ena/VASP protein into a bacterial or mammalian expression vector, introducing the vector into an appropriate host cell, expressing the altered Ena/VASP protein, and testing for a functional capability of the Ena/VASP proteins as disclosed herein.

In addition to being linked to a plasma membrane targeting compound (or intracellular targeting compound in other embodiments) the Ena/VASP binding molecules may be linked to a specific cell or tissue targeting molecule. A cell or tissue targeting molecule is any molecule or compound which is specific for a particular cell or tissue and which can be used to direct the Ena/VASP protein or nucleic acid to the cell or tissue. In some embodiments the cell or tissue targeting molecule is a molecule which specifically interacts with a cancer cell or a tumor. For instance, the cell or tissue targeting molecule may be a protein or other type of molecule that recognizes and specifically interacts with a tumor antigen.

Tumor-antigens include Melan-A/M A RT-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS 1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, 1 mp-1, EBV-encoded nuclear antigen (EBNA)-1, and c-erbB-2. These antigens as well as others are disclosed in PCT Application PCT/US98/18601.

In other embodiments the cell or tissue targeting molecule is a molecule which specifically interacts with an immune cell, a nerve cell, or a fibroblast. Cell surface antigens on each of these cells are well known in the art.

One of ordinary skill in the art is enabled to produce substantially pure preparations of any of the Ena/VASP proteins by standard technology, including recombinant technology, direct synthesis, mutagenesis, etc. As used herein, the term "substantially pure" means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations.

The mammalian cells may be treated in vivo, in vitro, or ex vivo. Thus, the cells may be in an intact subject or isolated from a subject or alternatively may be an in vitro cell line. A "subject" as used herein refers to a human or non-human mammal including but not limited to primates, dogs, cats, horses, sheep, goats, cows, rabbits, pigs and rodents.

Alternatively mammalian cell migration can be induced or increased by depleting the cell of functional Ena/VASP proteins. The discovery that mammalian cell migration can be induced by depleting the cell of functional Ena/VASP protein has important implications for regeneration of tissue, including, for instance would healing and neuroregeneration, or prevention or treatment of neurodegenerative disease.

A "wound" as used herein, means a trauma to any of the tissues of the body, especially that caused by physical means. The wound healing process involves a complex cascade of biochemical and cellular events to restore tissue integrity following an injury. The wound healing process is typically characterized by four stages: 1) hemostasis; 2) inflammation; 3) proliferation; and 4) remodeling. The inhibitors of the invention are useful for promoting wound healing by promoting cellular migration and thus remodeling. In one aspect, the methods of the invention are useful for treating a wound to the dermis or epidermis, e.g., a burn or tissue transplant, injury to the skin.

The methods of the invention may be used in the process of wound healing as well as tissue generation. When the methods of the invention are used to promote wound healing, cells may be manipulated to alter Ena/VASP activity in vitro and then added to the site of the wound or alternatively the cells present at the site of the wound may be manipulated in vivo to alter the activity of the Ena/VASP proteins in order to promote cellular movement. When the methods are used to promote tissue generation cells can be manipulated and grown in vitro on a scaffold and then implanted into the body or alternatively the scaffold may be implanted in the body, or it may be a naturally occurring scaffold and cells manipulated in vivo or in vitro can be used to generate the tissue.

In another aspect the invention involves methods for tissue regeneration, which are particularly applicable to neuronal cells. Thus the invention contemplates the treatment of subjects having or at risk of developing neurodegenerative disease in order to cause neuroregeneration. Neuronal cells are predominantly categorized based on their local/regional synaptic connections (e.g., local circuit interneurons vs. longrange projection neurons) and receptor sets, and associated second messenger systems. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, proprioceptive neurons (in the trigeminal mesencephalic nucleus), ciliary ganglion neurons (in the parasympathetic nervous system), etc. A person of ordinary skill in the art will be able to easily identify neuronal cells and distinguish them from non-neuronal cells such as glial cells, typically utilizing cell-morphological characteristics, expression of cell-specific markers, secretion of certain molecules, etc. Ena/VASP proteins have been identified in neuronal growth cones. The discovery that Ena/VASP proteins are negative regulators of cell motility indicates that Ena/VASP proteins are playing a role in the negative regulation of growth cones as well as in neuronal cell migration.

"Neurodegenerative disorder" is defined herein as a disorder in which progressive loss of neurons occurs either in the peripheral nervous system or in the central nervous system. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor). and Wernicke-Korsakoff's related dementia. Neurodegenerative diseases affecting sensory neurons include Friedreich's ataxia, diabetes, peripheral neuropathy, and retinal neuronal degeneration. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

Most of the chronic neurodegenerative diseases are typified by onset during the middle adult years and lead to rapid degeneration of specific subsets of neurons within the neural system, ultimately resulting in premature death. The Ena/VASP protein inhibitor may be administered to a subject to treat or prevent neurodegenerative disease or to promote tissue generation or wound healing alone or in combination with the administration of other therapeutic compounds for the treatment or prevention of these disorders or promotion of tissue generation or wound healing.

Antiparkinsonian agents include but are not limited to Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinelorane Hydrochloride; Ropinirole Hydrochloride; Selegiline Hydrochloride; Tolcapone; Trihexyphenidyl Hydrochloride.

Drugs for the treatment of amyotrophic lateral sclerosis include but are not limited to Riluzole.

Drugs for the treatment of Paget's disease include but are not limited to Tiludronate Disodium.

Drugs for the treatment of Wound healing include but are not limited to Ersofermin.

An "Ena/VASP inhibitor" as used herein is any compound which prevents the activity of Ena/VASP proteins. Ena/VASP inhibitors include but are not limited to an Ena/VASP binding molecule conjugated to an intracellular targeting domain and Ena/VASP antisense molecules, and Ena/VASP dominant negative proteins.

An "intracellular targeting compound" as used herein refers to any molecule or compound which is specific for an intracellular membrane of a particular cell and which can be used to direct the Ena/VASP protein or nucleic acid to the intracellular membrane, e.g., mitochondrial, nuclear, lysosomal membrane. For instance the intracellular membrane targeting compound may be an amino acid sequence which extends across the membrane; a lipid membrane retention compound which associates with the lipids of the cell surface membrane, or a non-peptide targeting compound which associates with the proteins or lipids.

Nuclear targeting compounds can consist of a short peptide (typically from four to eight amino acid residues) that is rich in the positively charged amino acids lysine and arginine and usually contains proline. Mitochondria are double-membrane-bounded organelles that specialize in the synthesis of ATP-by electron transport and oxidative phosphorylation. Most of their proteins are encoded by the cell nucleus and imported from the cytosol. Mitochondria have four subcompartments: the matrix space; the inner membrane; the intermembrane space; and the outer membrane that face the cytosol. Each of these subcompartments contains a distinct set of proteins to which the mitochondrial targeting sequence can bind. These targeting sequences, if they are peptides, usually are 12–80 residues long. Mitochondrial targeting sequences have been described, e.g., the amino-terminal 31 amino acids of the precursor of sub-unit VIII of cytochrome c oxidase forms a mitochondrial targeting sequence.

As mentioned above, the Ena/VASP inhibitors embrace antisense oligonucleotides that selectively bind to an Ena/VASP nucleic acid molecule, to reduce the expression of Ena/VASP. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the sequences of nucleic acids encoding Ena/VASP proteins, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative MRNA splicing occurs. In addition, the antisense is targeted, preferably, to sites in which mRNA secondary structure is not expected (see, e.g., Sainio et al, *Cell Mol. Neurobiol.* 14(5):439–457, 1994) and at which proteins are not expected to bind. Finally, although the listed sequences are cDNA sequences, one of ordinary skill in the art may easily derive the genomic DNA corresponding to the cDNA of an Ena/VASP protein. Thus, the present invention also provides for antisense oligonucleotides which are complementary to the genomic DNA corresponding to nucleic acids encoding Ena/VASP proteins. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding Ena/VASP proteins, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art, as further described below.

The invention also provides, in certain embodiments, "dominant negative" polypeptides derived from Ena/VASP proteins. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative Ena/VASP polypeptide in a cell is a reduction in function of active Ena/VASP proteins. One of ordinary skill in the art can assess the potential for a dominant negative variant of a protein, and using standard mutagenesis techniques to create one or more dominant negative variant polypeptides. For example, given the teachings contained herein of Ena/VASP proteins, especially those which are similar to known proteins which have known activities, one of ordinary skill in the art can modify the sequence of the Ena/VASP proteins by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art. Thus dominant negative Ena/VASP proteins are Ena/VASP inhibitors of the invention.

In other aspects the invention relates to methods of altering learning and memory. Several methods have been described in the prior art for treating learning and memory disorders. For instance, U.S. Pat. No. 5,488,049 issued to Costa et al. is directed to the treatment of learning and memory disorders using benzothiadiazide derivatives as nootropic agents. Other references have described the use of cholinergic agonists to enhance learning and memory. Studies have shown that in dementias, there is a marked loss of cholinergic neurons which mediate transmission to the neocortex and hippocampus which is correlated with memory defects (Bartus et al, 1982, *Science* 217, 408–41 7). Cholinergic antagonists such as scopolamine were shown to interfere with memory in animal studies (Spencer & Lal, 1983, *Drug. Dev. Res.*, 3, 489–502). The amino acid L-glutamate is the principal excitatory neurotransmitter in the mammalian CNS. This neurotransmitter exerts its effects by activating ionotropic and metabotropic receptors located on the dendrites and soma of neurons and glial cells. A number of compounds that bind to these three types of ionotropic glutamate receptors have been demonstrated to facilitate or inhibit memory and learning processes in animals and humans. Decrements in cognitive abilities associated with normal aging and with age-related disorders such as Alzheimer's disease are associated with decreases in cholinergic neurotransmission (Bartus R et al. (1982) *Science* 217:408–417; Mash Det al. (1985) *Science* 228:1115–1117)

Ena/VASP proteins, in particular Ev1, have been identified in neuronal synapses. It is known that synapses are remodeled during the processes of learning and memory. Without being limited to a particular mechanism, it is believed that Ena/VASP modulators can contribute to variations in neurotransmission that result in alterations in memory and learning processes by altering synapse remodeling. It has been discovered according to the invention that Ena/VASP inhibitors can enhance memory and learning and that activators interfere with these processes.

The present invention therefore provides a method of treating impaired memory or a learning disorder in a subject, as well as, impaired memory or learning which is age-associated, is consequent upon electro-convulsive therapy or which is the result of brain damage caused, for example, by stroke, an anaesthetic accident, head trauma, hypoglycemia, carbon monoxide poisoning, lithium intoxication or a vitamin deficiency. The present compounds can thus be used in the therapeutic treatment of clinical conditions in which memory defects or impaired learning occur as well as to simply improve memory or learning whenever it is desirable.

Memory defects occur with several kinds of dementia such as Alzheimer's disease, senile dementia, multi-infarct dementia (MID), a senile dementia caused by cerebrovascular deficiency, and the Lewy-body variant of Alzheimer's disease with or without association with Parkinson's disease. Creutzfeld-Jakob disease is a rare dementia with which memory disorders are associated. Loss of memory is also common feature of brain-damaged patients. Brain damage may occur, for example, after a classical stroke or as a result of an anaesthetic accident, head trauma, hypoglycemia, carbon monoxide poisoning, lithium intoxication, vitamin (B 1, thiamine and B 12) deficiency, or excessive alcohol use. Korsakow's disorder is a rare memory disorder which is characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy (ECT).

Learning and memory can be improved using Ena/VASP inhibitors. The effectiveness of these inhibitors can be tested in animal models. The available animal models of memory loss and impaired learning involve measuring the ability of animals to remember a discrete event. The passive avoidance procedure is the most widely used test. Here, the animal remembers the distinctive enviroument in which a mild electric shock is delivered and avoids it on a second occasion. However, this test has several disadvantages. A variant of the passive avoidance procedure therefore makes use of a rodent's preference for dark enclosed environments over light open ones, but shock is not used. Movement from a light box to a dark one has been used as a test for anxiolytic drugs in mice: Crawley, J. N., 1981, *PharmacoL Biochem. Behav.*, 15, 695–699; Costall, B. et al, 1987, *Neuropharmacol.*, 26, 195–200; Costall, B. et al, 1989, *Pharmacol. Biochem. Behav.*, 32, 777–785. The test is thought to capitalize on the conflict between exploratory drive and fear of unknown environments. In another test the dark box is remembered on a second occasion as a "safe " place and there is less hesitation about entering. Barnes, J. M. et al, 1989, *Br. J. Pharmacol.*, 98 (Suppl) 693P; Barnes, J. M. et al, 1990, *Pharmacol. Biochem. Behav.*, 35, 955–962. Other tests include the Randt Memory Test (Randt et al., *Clin. Neuropsychol.*, 1980, 2: 184), Wechsler Memory Scale (*J Psych.* 19:87–95 (1945), Forward Digit Span test (Craik, Age Differences in Human Memory, in: *Handbook of the Psychology of Aging*, Birren, J., and Schaie, K. (Eds.), New York, Van Nostrand (1977), Mini-Mental State Exam (Folstein et al., *J. ofPsych. Res.* 12:189–192 (1975), or California Verbal Learning Test (CVLT). The Ena/VASP inhibitors of the invention can be combined with other drugs for enhancing memory and learning. For instance, the compound piracetam has been prescribed for treatment to enhance memory (Giurgea et al, *Arch. Int. Pharmacodyn. Ther.*, 166, 238 (1967)). U.S. Pat. No. 4,639,468 to Roncucci et al describes the compound milacemide which is mentioned as useful for treatment of memory troubles. Further investigations of milacemide have documented the memory-enhancing capabilities of milacemide in human subjects (B. Saletu et al, *Arch. Gerontol. Geriatr., S*, 165–181 (1986)). A variety of other compounds have also been found to be useful, including vasoactive compounds, TRH and analogues, 5-HT$_3$ antagonists (e.g. ondansetron, referred to above), central stimulants, ACE inhibitors, opiate and dopamine antagonists, benzodiazepine receptor antagonists, ACTH analogues and alpha agonists. Aniracetam and related pyrrolidinone derivatives, by acting preferentially as positive allosteric modulators of AMPA receptor function, increase the strength of synaptic responses elicited by electrical stimulation of excitatory affferents to CA1 hippocampal pyramidal neurons attenuating AMPA receptor spontaneous desensitization (6) and enhancing learning and memory (nootropic action) in animals. Cognition adjuvants include but are not limited to Ergoloid Mesylates; Piracetam; Pramiracetam Hydrochloride; Pramiracetam Sulfate; Tacrine Hydrochloride. Cognition enhancers include but are not limited to Besipirdine Hydrochloride; Linopirdine; Sibopirdine . Memory adjuvants include but are not limited to Dimoxamine Hydrochloride; Ribaminol. Mental performance enhancers include but are not limited to Aniracetam.

In general the Ena/VASP inhibitors are delivered to the brain in order to enhance memory and learning. They can be delivered to the brain using any known route of administration as long as they ultimately are delivered to brain cells. In one method of direct delivery the compounds may be directly injected into the brain, or they may be delivered systemically in combination with a means for temporarily permeabilizing the blood-brain barrier. In other methods the compounds can be (i) infused into the brain, (ii) genetically engineered cells can be implanted in the brain, and (iii) the compounds can be altered to cross the blood-brain barrier.

In other aspects the invention relates to methods of reducing memory and learning by activating Ena/VASP proteins in a neuron. It is sometimes useful to reduce memory and learning after a traumatic event. The Ena/VASP activators can be combined with other drugs which reduce learning and memory. Ketamine, phencyclidine, and even more potently, dizocilpine (MK-801), which are allosteric NMDA receptor antagonists, produce profound alterations in learning, disrupt memory consolidation and retrieval in animals and man, thereby eliciting a psychotic syndrome resembling schizophrenia in humans.

The invention also contemplates delivery of nucleic acids, polypeptides or non-peptide compounds i.e., mimetics for therapeutic purposes. Delivery of polypeptides and non-peptide compounds can be accomplished according to standard drug delivery protocols which are well known in the art. In another embodiment, the delivery of nucleic acid is accomplished by ex vivo methods, i.e. by removing a cell from a subject, genetically engineering the cell to include an Ena/VASP protein, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). A modified ex vivo method is particularly preferred when it is desirable to promote wound healing or tissue generation. This modified method involves genetic manipulation of cells which are not derived from the subject in which they will eventually be implanted. Numerous transfection and transduction techniques as well as appropriate expression vectors are well known to those of ordinary skill in the art, some of which are described in PCT application W095/00654. In vivo nucleic acid delivery using vectors such as viruses and targeted liposomes also is contemplated according to the invention.

In preferred embodiments, a virus vector for delivering a nucleic acid encoding an Ena/VASP protein is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220–227, 1996,; Eloit et al, *J. Virol.* 7:5375–5381, 1997,; Chengalvala et al., *Vaccine* 15:335–339, 1997), a modified retrovirus (Townsend et al, *J. Virol.* 71:3365–3374, 1997), a nonreplicating retrovirus (Irwin et al., *J. Virol.* 68:5036–5044, 1994), a replication defective Semliki Forest virus (Zhao et al., *Proc. Natl. Acad. Sci. USA* 92:3009–3013, 1995), canarypox virus and highly attenuated vaccinia virus derivative (Paoletti, *Proc. Natl. Acad. Sci. USA* 93:11349–11353, 1996), non-replicative vaccinia virus (Moss, *Proc. Natl. Acad. Sci. USA* 93:11341–11348, 1996), replicative vaccinia virus (Moss, *Dev. Biol. Stand.* 82:55–63, 1994), Venezuelan equine encephalitis virus (Davis et al., *J. Virol.* 70:3781–3787, 1996), Sindbis virus (Pugachev et al., *Virology* 212:587–594, 1995), and Ty virus-like particle (Allsopp et al., *Eur. J. Immunol* 26:1951–1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "*Gene Transfer and Expression, A Laboratory Manual,*" W. H. Freeman Co., New York (1990) and Murry, E. J. Ed. "*Methods in Molecular Biology,* " vol. 7, Humana Press, Inc., Clifton, N.J. (1991).

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids into cells, depending on whether the nucleic acids are introduced in vitro or in vivo in a host. Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a cell or tissue targeting molecule attached thereto, such as those described above. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

When administered, the therapeutic compositions of the present invention can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, pulmonary, intravenous, intraperitoneal, intrarectal, intraocular, intramuscular, intracavity, subcutaneous, or transdermal. Techniques for preparing aerosol delivery systems containing active agents are well known to those of skill in the art. Generally, such systems should utilize components which will not significantly impair the biological properties of the active agents (see, for example, Sciarra and Cutie, "Aerosols, " in *Remington's Pharmaceutical Sciences,* 18th edition, 1990, pp 1694–1712; incorporated by reference). Those of skill in the art can readily determine the various parameters and conditions for producing aerosols without resort to undue experimentation. When using antisense preparations, intravenous or oral administration are preferred.

The compositions of the invention are administered in effective amounts. An "effective amount " is that amount of an Ena/VASP composition that alone, or together with further doses, produces the desired response, e.g. increases or decreases expression or activity of an Ena/VASP molecule. The term "Ena/VASP composition " is used synonymously with the terms "active compound","active agent " or "active composition" and as used herein refers to any of the active compounds of the invention which produce a biological effect, e.g., Ena/VASP activators, inhibitors, etc. In the case of treating a particular disease or condition characterized by increased cell motility, such as cancer metastasis, the desired response is inhibiting the cellular motility and thus the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of Ena/VASP composition for producing the desired response in a unit of weight or volume suitable for administration to a patient. The response can, for example, be measured by determining the effect on cell motility following administration of the Ena/VASP composition via a reporter system by measuring downstream effects such as increased cell motility in vivo, or by isolating cells and measuring cellular migration in vitro or Ena/VASP cellular localization, or by measuring the physiological effects of the Ena/VASP composition, or decrease of disease symptoms. Other assays will be known to one of ordinary skill in the art and can be employed for measuring the level of the response.

The doses of the active compounds (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or altering cell motility, doses of an Ena/VASP composition are formulated and administered in doses between 1 ng and 1 mg, and preferably between 10 ng and 100 μg, according to any standard procedure in the art. Where nucleic acids encoding an Ena/VASP protein or variants thereof are employed, doses of between 1 ng and 0.1 mg generally will be formulated and administered according to standard procedures. Other protocols for the administration of Ena/VASP compositions will be known to one of ordinary skill in the art, in which the dose amount, schedule of injections, sites of injections, mode of administration (e.g., intra-tumoral) and the like vary from the foregoing. Administration of Ena/VASP compositions to mammals other than humans, e.g. for testing purposes or veterinary therapeutic purposes, is carried out under substantially the same conditions as described above.

When administered, the pharmaceutical preparations of the invention are applied in pharmaceutically-acceptable amounts and in pharmaceutically-acceptable compositions. The term "pharmaceutically acceptable " means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

An Ena/VASP composition may be combined, if desired, with a pharmaceutically-acceptable carrier. The term "pharmaceutically-acceptable carrier " as used herein means one or more compatible solid or liquid fillers, diluents or encapsulating substances which are suitable for administration into a human. The term "carrier " denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of Ena/VASP composition, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

Screening assays for identifying potential drug candidates (and lead compounds) and determining the specificity's thereof are also provided according to the invention. For example, putative Ena/VASP binding compounds can be identified by screening libraries and the other methods described above. Knowing that a putative compound (peptide or non-peptide) interacts with Ena/VASP proteins, one can determine whether this compound is a drug that can exert a biological effect on cellular migration, e.g., either as an activator or as an inhibitor by using any of the screening assays of the invention. The compounds which are identified using these screening assays are known as "lead " compounds. These lead compounds are then put through further testing, including, eventually, in vivo testing in animals and humans, from which the promise shown by the lead compounds in the original in vitro tests is either confirmed or refuted. See *Remington's Pharmaceutical Sciences,* 1990, A. R. Gennaro, ed, Chapter 8, pages 60–62, Mack Publishing Co., Easton, Pa.; Ecker and Crooke, 1995, *Bio/Technology* 13:351–360.

The invention also encompasses assay kits which can be useful in the screening of putative Ena/VASP binding compounds. In a particular embodiment of the present invention, an assay kit is contemplated which comprises in one or more containers (a) an Ena/VASP activator or inhibitor; and (b) an Ena/VASP binding protein such as an antibody for detecting the intracellular localization of Ena/VASP. The kit optionally further comprises instructions for a determining whether a putative activator or inhibitor is an actual activator or inhibitor by determining whether the putative compound reduces or enhances cellular migration, respectively.

Either of the putative activators or inhibitors or the Ena/VASP binding protein may be labeled in some embodiments. A wide range of labels can be used according to the invention, including but not limited to biotin, a fluorogen, an enzyme, an epitope, a chromogen, or a radionuclide. The method for detecting the label will depend on the nature of the label and can be any known in the art, e.g., film to detect a radionuclide; an enzyme substrate that gives rise to a detectable signal to detect the presence of an enzyme; antibody to detect the presence of an epitope, etc.

Another screening assay of the invention involves screening one or more putative compounds for the ability to interact with an actin barbed end to identify an actin binding molecule, and determining the effect of the actin binding molecule on cellular migration to determine whether the actin binding molecule is a therapeutic compound for inhibiting or promoting cellular migration. The invention also includes compositions identified by the screening method.

The invention also encompasses a modified cell which is an Ena/VASP negative cell. The cell is any type of cell in which the expression or activity of endogenous Ena/VASP proteins has been reduced relative to the amount of Ena/VASP ordinarily expressed in the cell. In some cases the expression or activity of Ena/VASP is completely eliminated from the cell. In some preferred embodiments the cell is a Mena/VASP double negative cell. The cells are useful for a variety of in vitro, in vivo, and ex vivo purposes. For instance, the cells can be used to screen for compounds that are capable of rescuing the cell from the Ena/VASP negative phenotype. These compounds may be useful for inhibiting completely or partially cellular migration. The cells may also be useful in vitro or ex vivo for tissue generation or regeneration.

A method for identifying a therapeutic compound for inhibiting cellular migration by utilizing the modified cell is also provided according to the invention. The method can be performed using a putative therapeutic compound. A putative therapeutic compound is any compound which may inhibit cellular migration. These compounds may be rationally designed or part of a standard library of molecules.

The invention also includes compound having an actin binding domain and a cell motility domain. The compound preferably does not include a Listeria motility domain. An actin binding domain is any compound, peptide, or nonpeptide that interacts with the barbed end of actin. Actin binding domains may be identified using routine procedures known in the art such as by screening libraries or compounds with the barbed end of actin. Alternatively the actin binding domain can be rationally designed using computer modeling and other techniques known in the art based on the peptide sequence corresponding to amino acids 411–429 of Mena. In some embodiments the actin binding domain is the peptide sequence corresponding to amino acids 411–429 of Mena or a conservative substitution thereof.

A cell motility domain is any compound, peptide, or nonpeptide that retains the cell motility modulation activity of Ena/VASP proteins. Cell motility domains may be identified using routine procedures such as the motility assays described in the examples below. Alternatively the cell motility domain can be rationally designed using computer modeling and other techniques known in the art based on the peptide sequence corresponding to amino acids 1–280 of Mena plus residues 345–541 or in some embodiments corresponding to amino acids 1–280. In some embodiments the cell motility domain includes a conserved EVH1 domain or is the peptide sequence corresponding to amino acids 1–280 of Mena or a conservative substitution thereof.

The invention also relates to modified forms of the Mena protein. For instance the invention includes a modified Ena/VASP protein having the amino acid sequence of the mature peptide of SEQ ID NO: 2 wherein at least one amino acid residue has been substituted and wherein the substitution is selected from the group consisting of (a) a non-conservative or conservative substitution of a serine residue corresponding to position 236 or 376 of SEQ ID NO: 2; (b) a non-conservative substitution or deletion of one or more residues corresponding to position 411–429 of SEQ ID NO: 2; (c) a conservative substitution of at least one residue corresponding to position 281–344 of SEQ ID NO: 2; (d) a non-conservative substitution or deletion of at least one residue corresponding to position 281–344 of SEQ ID NO: 2; and (e) a non-conservative or conservative substitution or deletion of one or more residues corresponding to position 411–429 of SEQ ID NO: 2.

EXAMPLES

Example 1

Introduction

To test the hypothesis that Ena/VASP proteins are positive regulators of cell motility, the effect of elevated levels of Mena or VASP on cell migration was analyzed. Rat2 fibroblasts were infected with a retrovirus that drives the expression of an EGFP (enhanced green fluorescent protein)—Mena fusion protein and analyzed using immunofluorescence microscopy; quantitative western blots of cell lysates from populations sorted for low, medium, or high levels of GFP signal; and with time-lapse videomicroscopy.

Methods

Molecular Cloning

Subcloning and polymerase chain reaction (PCR) were performed using standard methods. The full-length coding portion of the Mena cDNA (encoding amino acids 1–541 of SEQ ID NO: 2) was amplified by PCR and cloned in frame with EGFP (Clonetech Laboratories, Inc. Palo Alto, Calif.) as a C-terminal fusion. This fusion construct was subcloned into a replication-defective retroviral expression vector (pMSCV) to create the EGFP-Mena construct.

Retroviral Packaging, Infection, FACS sorting and Cell culture

Retroviral packaging was performed in Bosc23 cells (ATCC, Manassas, Va.) by $CaPO_4$ transfection of 6.7 µg retroviral plasmid and 2.3 µg pCL-Eco helper plasmid. Retroviral-containing supernatants were harvested and transferred to dishes containing Rat2 cells in the presence of 4 µg/mL polybrene for 16 hrs at 32° C. Within 48 hrs, cells were trypsinized and resuspended in PBS containing 5% fetal calf serum for FACS sorting. GFP[+] cells were sorted into a collection tube containing complete media and re-plated under standard conditions. Freezer stocks of sorted cells were prepared the next day. All experiments were conducted within 2 passages after thawing a fresh aliquot of cells. General cell culture was performed using standard methods. Rat2 (ATCC, Manassas, Va.) and Bosc23 cells were grown in DME supplemented with 10% fetal calf serum and L-glutamine in a 5% humidified $CO_2$ atmosphere at 37° C. 24 hours before videomicroscopy experiments, cells were adapted to $CO_2$-independent microscopy media that consisted of reconstituted DME (Life Technologies, Inc. Rockville, Md.) containing 4500 g/L glucose, 0.35 g/L sodium bicarbonate, 25 mM HEPES, 10% fetal calf serum and L-glutamine (2 mM).

Immunofluorescence Microscopy

Rat2 cells (ATCC, Manassas, Va.) were plated and allowed to spread for 1.5–2 hours on acid-washed glass coverslips that had been coated overnight at 4° C. with 10 µg/mL fibronectin (Becton Dickinson, Franklin Lakes, N.J.). Cells were fixed with ice-cold 4% paraformaldehyde in PBS for 10 minutes at room temperature. Cells were washed twice with PBS and then permeabilized with 0.2% Triton X-100 in PBS for 3 minutes and washed two more times with PBS. Coverslips were blocked for 30 minutes in 5% BSA (RIA grade)/5% normalized Donkey serum in PBS. All subsequent antibody steps were incubated in 1% BSA/PBS for at least 30 minutes and washes were in PBS. Anti-Mena polyclonal antisera (2197, produced by Gertler laboratory) was used at 1:400, anti-VASP polyclonal antisera (M4, Alexis Corporation, San Diego, Calif.) was used at 1:400, coumarin-phallicidin (Molecular Probes Inc., Eugene, Oreg.) was used at 1:20, anti-vinculin monoclonal antibody (F7g, a kind gift from K. Burridge) was used at 1:20. All secondary antibodies (Texas Red-, Cy5-Donkey anti-rabbit or anti-mouse, Jackson ImmunoResearch Laboratories, Inc., West Grove, Pa.) were used at 1:500. Coverslips were mounted with Fluoromount G (Electron Microscopy Sciences, Fort Washington, Pa.) and viewed on a Zeiss Axiophot microscope equipped with a Deltavision imaging and software system (Applied Precision Inc., Issaquah, Wash.).

Quantitative Western Blots

RIPA lysates were prepared according to Harlow and Lane (1999) *Using Antibodies: a Laboratory Manual.* Cold Spring Harbor, N.Y. Cold Spring Harbor Laboratory press. Protein content of samples was quantitated using the BCA kit (Pierce Chemical Company, Rockford, Ill.). 7.5 µg of lysate protein was separated under standard SDS-PAGE conditions and transferred to PVDF membrane for blotting. Membranes were blocked, incubated with anti-Mena antisera (2197, 1:5000) and processed with chemifluoresent reagents (ECF kit, Amersham Pharmacia Biotech, Piscataway, N.J.). Blots were scanned and quantitated using a FluorImager instrument and ImageQuant software (Molecular Dynamics, Sunnyvale, Calif.). All blots contained a dilution series of purified Mena protein to ensure that the observed signals were within the linear range of detection. Fold overexpression numbers represent total Mena immunoreactive signal (endogenous protein and EGFP-Mena fusion protein) relative to uninfected control cells.

Videomicroscopy, Cell tracking and Data Analysis

Cells adapted to microscopy media (Life Technologies, Rockville, Md.) as described above were trypsinized, counted, and resuspended in microscopy media at $7.14 \times 10^3$ cells/mL. 1.4 mL (10,000 cells) of this cell suspension was added to a ΔT dish (Bioptechs Inc., Butler, Pa.) that had previously been coated overnight with 10 µg/mL fibronectin (Becton Dickinson) at 4° C. and then blocked with lmg/mL cell-culture-grade BSA (Sigma, St. Louis, Mo.). Cells were allowed to attach and spread for 1 hour at 37° C. before movies were initiated. 10x phase contrast movies were 4.5 hours long with a frame taken every five minutes. A custom time-lapse collection script written in IPLabs was used to automate microscope and camera function. Light was shutter controlled. Movies were considered analysis-quality if there were no focus or bubble problems and cells remained alive and dividing throughout the experiment. Once a movie met the quality control criteria, it was transferred into the image analysis program DIAS (Solltech, Inc., Oakdale, Iowa.) and cells were outlined using the Trace on Movie command. All cells were outlined that remained entirely within the field of view, did not more than transiently touch other cells and did not divide. Cell paths were generated from the calculated centroid positions and parameters (speed and membrane flow) were calculated from the resulting path file. Speed was calculated using the Central Difference Method in DIAS, which is equivalent to a root mean squared calculation. Raw data from the DIAS program was transferred to Excel (Microsoft, Redmond, Wash.) for tabulation, DeltaGraph (DeltaPoint Inc., Monterey, Calif.) for plotting and Minitab (Minitab Inc., State College, Pa.) for statistical analysis.

Results

When these cells were examined, the GFP signal distribution corresponded to the distribution of endogenous Mena in uninfected cells. In addition, F-actin distribution was not detectably altered by overexpression of the fusion protein. Because EGFP-Mena was expressed from a stably integrated provirus, cells could be sorted by FACS into populations that contained increasing amounts of the fusion protein as detected by GFP signal. Cell lysates from populations sorted for low, medium, or high levels of GFP were prepared and analyzed by quantitative western blotting using an anti-Mena antiserum. The low, medium, and high overexpressing populations contained a total of 1.9-, 2.7-, and 3.9-fold more Mena, respectively, than the uninfected Rat2 controls. The fold overexpression numbers were determined from chemifluorescent quantification using a FluorImager (Molecular Dynamics, a subsidiary of Amersham Pharmacia Biotech, Uppsala, Sweden).

To address the effect of EGFP-Mena overexpression on cell motility, cells were analyzed by time-lapse videomicroscopy. Movies of migrating cells were digitized to allow outlines of the cells to be traced and the centroid position of the cells to be calculated using image-analysis software. Cell speed was calculated from the paths of cells. Cells were tested within two passages of sorting to reduce any possible phenotypic drift associated with compensation mechanisms such as the up- or downregulation of other adhesion or motility genes. Even after five passages, these cells showed no downregulation of VASP by western blot. Completely opposite to the predicted increase in motility, cell speeds decreased with increasing levels of EGFP-Mena expression. This is illustrated in FIG. 1, which provides box and whisker plots of speed and FIG. 3a, which diagrams cell-path migrations over time. In addition, the cells overexpressing the highest levels of EGFP-Mena showed a distinct lack of polarity. Similar results were obtained using a retroviral construct to overexpress an untagged VASP protein, indicating that VASP overexpression has a similar effect on motility and that the EGFP-Mena phenotype is not simply due to the EGFP tag. Therefore, increased levels of Mena or VASP act to retard fibroblast motility and the overexpression of EGFP-Mena inhibits cell motility in a dose-responsive manner.

Example 2

Introduction

Figure 2:
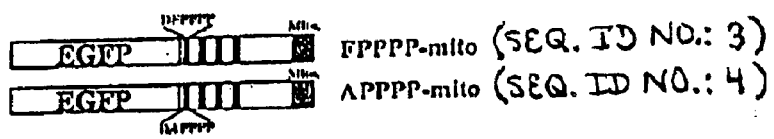
FIG. 2: Expression of a mitochondrially targeted Ena/VASP-binding protein sequesters all Mena and VASP, but leaves other focal adhesion proteins in place.

To test the hypothesis that sequestration of Ena/VASP proteins on the mitochondria increases cell speed, the Ena/VASP function was specifically blocked by exploiting the ability of the EVH1 domain to target Ena/VASP proteins within cells thereby sequestering all Ena/VASP proteins on the mitochondrial surface. Previous work has demonstrated that ActA is targeted to the outer surface of mitochondrial membranes when expressed in eukaryotic cells (Pistor, S., Chakraborty, T., Niebuhr, K., Domann, E., and Wehland, J. (1994). *The ActA protein of Listeria monocytogenes acts as a nucleator inducing reorganization of the actin cytoskeleton. Embo J.* 13, 758–53). This observation was exploited to map the binding site for VASP and actin-nucleation domains within ActA (Pistor, S., Chakraborty, T., Walter, U., and Wehland, J. (1995). *The bacterial actin nucleator protein ActA of Listeria monocytogenes contains multiple binding sites for host microfilament proteins. Curr Biol* 5,517-25); utilizing portions of ActA to create a construct that directs a fusion between enhanced green fluorescent protein (EGFP) and four Ena VASP Homology (EVH1)-binding sites (D/E FPPPPXDDE) (SEQ ID NO: 1) to the surface of the mitochondria. It is important to point out that this construct lacks all the amino terminal sequences in ActA, including those shown to activate the Arp2/3 complex and drive actin nucleation, and simply acts to place EVH1 binding sites on the mitochondrial surface. A parallel construct was made in which the phenylalanine residue, known to be essential for EVH 1-binding (Carl, U D., Pollmann, M., Orr, E., Gertler, F. B., Chakraborty, T., and Wehland, J. (1999). *Aromatic and basic residues within the EVH1 domain of VASP specify its interaction with proline-rich ligands. Curr Biol* 9, 715–8; Niebuhr, K., Ebel, F., Frank, R., Reinhard, M, Domann, E., Carl, U. D., Walter, U., Gertler, F. B., Wehland, J., and Chakraborty, T (1997). *A novel proline-rich motif present in ActA of Listeria monocytogenes and cytoskeletal proteins is the ligand for the EVH1 domain, a protein module present in the Ena/VASP family. Embo J.* 16, 5433–44), was changed to an alanine in each of the four FPPPP (SEQ ID NO: 3) repeats. This construct, "APPPP-mito " (SEQ ID NO: 4), does not bind Ena/VASP proteins, but contains all of the other sequence present in the original construct to serve as a specificity control for Ena/VASP-independent effects. A diagram of both mito-targeting constructs is shown in FIG. 2a. Rat2 cells were infected with retroviruses that express these fusion proteins, and after infection these cells were sorted by FACS into populations of cells that were >98% GFP+ and expressed equivalent levels of the FPPPP-mito (SEQ ID NO: 3) or APPPP-mito (SEQ ID NO: 4) constructs as assessed by GFP signal.

Methods

For descriptions of molecular cloning, retroviral packaging, infection, FACS sorting, cell culture, immunofluorescence microscopy, and time-lapse videomicroscopy see Example 1, Methods Section.

Mito Construct Production

Portions of the wild-type Listeria monocytogenes actA gene were amplified and cloned in frame with EGFP as C-terminal fusions. An equivalent portion of a mutant version of the actA gene (in which each of the phenylalanine residues in the FPPPP (SEQ ID NO: 3) repeats was changed to alanine, a kind gift from S. Pistor, GBF, Braunschweig, Germany) was used in the creation of the APPPP (SEQ ID NO: 4) version. The FPPPP-(SEQ ID NO: 3) and APPPP-mito (SEQ ID NO: 4) constructs contain a portion of the gene that encodes amino acids 231–610 of SEQ ID NO: 5 (numbering excludes signal sequence). A separate set of constructs in which the FPPPP (SEQ ID NO 3) repeats were fused directly to the mitochondrial targeting sequence (amino acids 231–360 and 590–610 of SEQ ID NO: 5) behaves identically to the original mito constructs. The FPPPP-(SEQ ID NO: 3) and APPPP-(SEQ ID NO: 4) constructs were subcloned into the same retroviral vector as EGFP-Mena.

Results

The distribution of Ena/VASP proteins in the FPPPP-mito (SEQ ID NO: 3) expressing cells was analyzed by immunofluorescence. Instead of the normal focal adhesion and membrane localization, all the detectable Mena or VASP signals were co-localized with the GFP signal on the mitochondria The results are illustrated in FIG. 2b. As expected, the APPPP-mito (SEQ ID NO: 4) cells showed GFP-labeled mitochondria, but the Mena signal was distributed normally in focal adhesions and the leading edge with little or no overlap with the mitochondria. VASP also showed no co-localization with the mitochondria in the APPPP-mito (SEQ ID NO: 4) cells. EVL expression is not detectable by immunofluorescence in Rat2 cells, so anti-EVL staining was not performed on the FPPPP-mito (SEQ ID NO: 3) cells. If EVL is expressed at low levels in Rat2 cells, it would likely be sequestered on the mitochondrial surface as well since expression of the FPPPP-mito (SEQ ID NO: 3) construct in T-cells, which express high levels of EVL, results in quantitative recruitment of EVL to the mitochondrial surface. Interestingly, the diffuse cytoplasmic signal was not detected for Mena in the FPPPP-mito (SEQ ID NO: 3) cells, which was demonstrated by comparing the Mena staining in cell expressing APPPP-mito (SEQ ID NO: 4) to the cell expressing FPPPP-mito (SEQ ID NO: 3). This suggests that a pool of Mena protein exists in the cytosol that is not associated with the focal adhesions or leading edge under normal circumstances. Together, these results indicate that the FPPPP-mito (SEQ ID NO: 3) construct effectively depletes all detectable Mena and VASP protein within cells from the leading edge, focal adhesions and cytosol and sequesters it on the mitochondrial surface.

The FPPPP-mito (SEQ ID NO: 3) expressing cells were stained with a series of markers to determine if mitochondrial sequestration of Ena/VASP proteins resulted in any detectable changes in focal adhesions or the actin cytoskeleton. As judged by phalloidin staining, all of the normal forms of F-actin for fibroblasts (stress fibers, ruffles, and microspikes) were present in the FPPPP-mito (SEQ ID NO: 3) cells and indistinguishable from the APPPP-mito (SEQ ID NO: 4) and parental control cells. Furthermore, no unusual enrichment of F-actin on or near the mitochondria was observed, indicating that clustering of endogenous Ena/VASP proteins in vivo is not sufficient to recruit or assemble detectable levels of F- actin at the mitochondria. In addition to this observation, the p34 component of the Arp2/3 complex was not detectably re-localized in the FPPPP-mito (SEQ ID NO: 3) cells. When the distributions of Mena and vinculin were examined in the FPPPP-mito (SEQ ID NO: 3) cells, vinculin remained in its normal location at focal adhesions and was not recruited to the mitochondria along with Mena. Other focal adhesion markers, including zyxin, tensin, FAK, paxillin, and phosphotyrosine, also showed normal distribution in these cells.

Figure 3A:
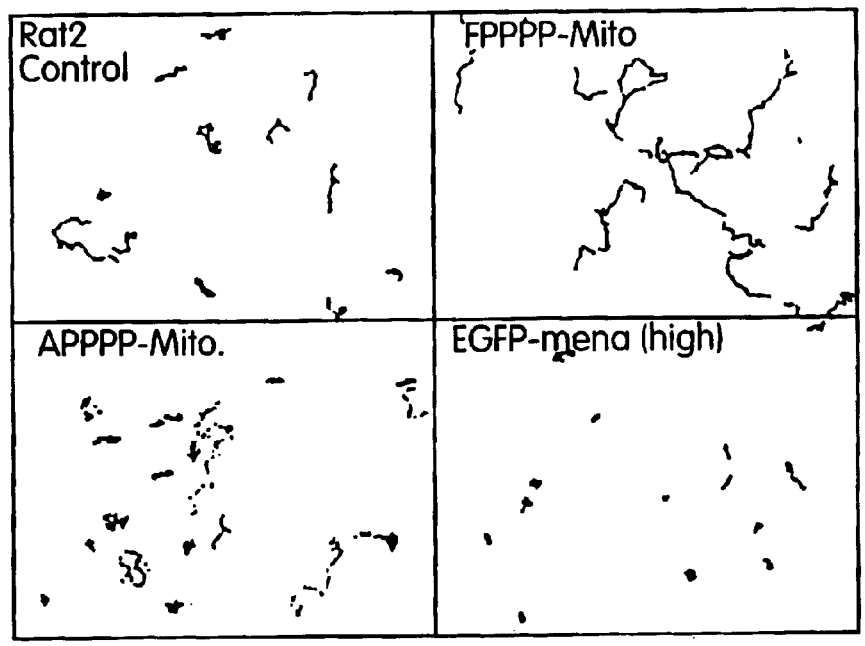
FIG. 3: Sequestration of Ena/VASP proteins stimulates cell motility. (a) Cell paths during a 4.5 hour random migration experiment. Dots show centroid positions at 5 minute intervals. (b) Box and whisker plots of cell speeds. Data was analyzed as in FIG. 1b (ANOVA p-value<0.0001). FPPPP is SEQ ID NO.: 3. APPPP is SEQ ID NO.: 4.
Figure 3B:
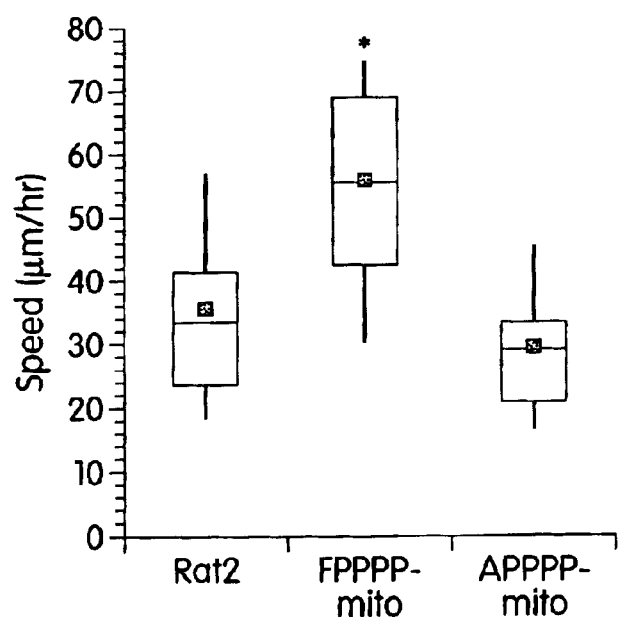

The FPPPP-mito (SEQ ID NO: 3) cells were analyzed by time-lapse video microscopy to determine if depletion of Mena and VASP from the leading edge and focal adhesions resulted in changes in cell motility. As illustrated in FIG. 3a, b the sequestration of all Ena/VASP protein on the mitochondria caused the cells to move significantly faster than either the uninfected controls or the APPPP-mito (SEQ ID NO: 4) cells. This is consistent with observations that overexpression of Mena inhibits cell movement. It should be noted that these cells showed no detectable upregulation of Mena or VASP by western blot even after five or more passages and appeared to grow and divide indistinguishably from the controls. This last result indicates that Ena/VASP proteins are apparently dispensable for the successful execution of cytokinesis. Taken together, these results provide compelling evidence that Mena and VASP are not required in focal adhesions or at the leading edge for cell movement, and speed increases when Mena and VASP are sequestered on the mitochondria and are not in their normal locations.

Example 3

Introduction

Cell-population analysis was undertaken to explore the hypothesis that focal adhesion formation and number are unaffected by overexpression or sequestration of Ena/VASP proteins. Because cell migration depends on adhesion as well as actin polymerization at the leading edge, the various cell populations were analyzed to determine if the assembly, morphology or distribution of focal adhesions was affected. EGFP-Mena overexpressing (the "high " population), FPPPP-mito (SEQ ID NO: 3) and control cells were each stained after complete spreading with a battery of focal adhesion markers (FAK, vinculin, paxillin, tensin, phosphotyrosine, and zyxin).

Methods

For descriptions of molecular cloning, retroviral packaging, infection, FACS sorting, cell culture, immunofluorescence microscopy, and time-lapse videomicroscopy see Example 1, Methods Section.

Results

Observation of the staining patterns revealed no qualitative differences in number or distribution of focal adhesions in any of the cell populations. When the numbers of vinculin- or zyxin-positive focal adhesions were counted, there were no significant differences between the different cell populations . The vinculin data is shown in Table 1. During the spreading process, equivalent numbers of zyxin-positive focal adhesions at 15 and 45 minutes were observed in all cell populations. The results indicate that focal adhesion formation and number are not effected by overexpression or sequestration of Ena/VASP proteins.

TABLE 1

Number of Focal Adhesions per Cell (±SD)

|  | Rat2 | EGFP-Mena (high) | DFPPPP-mito SEQ ID NO.: 12 | DAPPPP-mito SEQ ID NO.: 13 |
| --- | --- | --- | --- | --- |
| Vinculin+ | 86.6 ± 16.0 | 72.7 ± 14.4 | 79.5 ± 17.7 | 81.6 ± 13.9 |
| Zyxin+ | 79.6 ± 26 | 73.6 ± 20 | 75.8 ± 19 | 79.2 ± 29 |

Example 4

Introduction

Figure 4A:
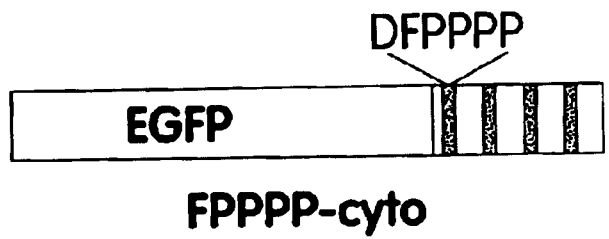
FIG. 4: Depletion of Ena/VASP proteins from focal adhesions, but not the leading edge, has no effect on cell motility. (a) Schematic diagram of cytoplasmic construct. (b) Box and whisker plots of cell speeds (p-value from student's t-test was>0.05). FPPPP is SEQ ID NO.: 3. DFPPPP is SEQ ID NO.:12.

The hypothesis that displacement of Ena/VASP proteins from focal adhesions, but not from the leading edge, has no effect on cell motility, was tested This was done using a slightly modified construct, illustrated in FIG. 4a, that contained GFP and the FPPPP (SEQ ID NO: 3) repeats but lacked the mitochondrial targeting sequence. This construct, FPPPP-cyto (SEQ ID NO: 3), is localized to the nucleus and cytoplasm and effectively displaces Mena and VASP from focal adhesions.

Methods

For descriptions of molecular cloning, retroviral packaging, infection, FACS sorting, cell culture, immunofluorescence microscopy, and time-lapse videomicroscopy see Example 1, Methods Section.

Cyto Construct Production

The FPPPP-cyto (SEQ ID NO: 3) and APPPP-cyto (SEQ ID NO: 4) constructs contain a portion of the actA gene that encodes amino acids 231–360. The FPPPP-cyto (SEQ ID NO: 3) and APPPP-cyto (SEQ ID NO: 4) constructs were subcloned into the same retroviral vector as EGFP-Mena. For description of basic mito construct production see Example 2, Methods Section.

Results

Interestingly, the FPPPP-cyto (SEQ ID NO: 3) cells retained distinct Mena staining at ruffles and the leading edge. As with the FPPPP-mito (SEQ ID NO: 3) construct, the F-actin and vinculin staining remained unchanged in FPPPP-cyto (SEQ ID NO: 3) cell populations. Cells expressing the negative-control version of this construct, APPPP-cyto (SEQ ID NO: 4), showed Mena staining indistinguishable from the controls. These results indicate that although recruitment of Ena/VASP proteins to focal adhesions requires interactions with FPPPP (SEQ ID NO: 3) containing proteins, targeting to the leading edge can occur by another mechanism.

Figure 4B:
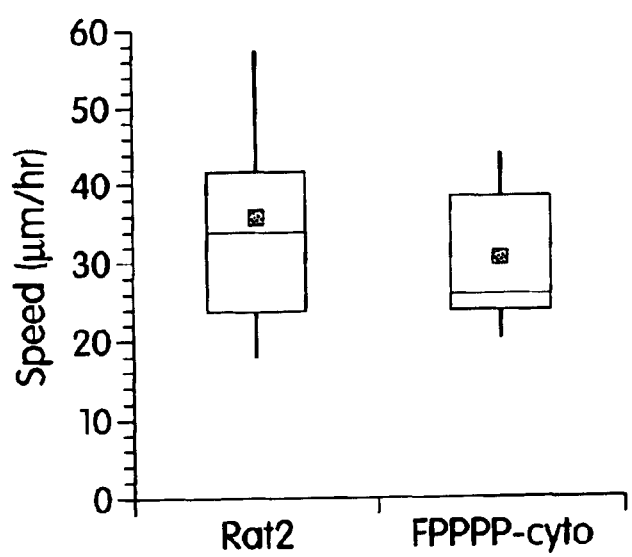

To test for effects on cell motility, populations of Rat2 cells expressing FPPPP-cyto (SEQ ID NO: 3) or the APPPP-cyto (SEQ ID NO 4) control constructs were analyzed by the videomicroscopy assay. The FPPPP-cyto (SEQ ID NO: 3) construct caused no change in cell speed, which is illustrated in FIG. 4b. Cells expressing APPPP-cyto (SEQ ID NO: 4) also did not differ significantly in their motility properties from the controls. These results indicate that displacement of Mena and VASP from focal adhesions has no effect on cell motility under the assay conditions. Therefore, the increased cell speeds observed in the FPPPP-mito (SEQ ID NO: 3) cells likely result from depletion of Mena and VASP from either the cytosol or leading edge, but not from focal adhesions.

Example 5

Introduction

To determine which part of the Mena molecule was responsible for leading edge localization, a construct was prepared that expressed just the EVH1 domain of Mena tagged with EGFP. The construct was introduced into Rat2 cells by retroviral transduction, and immunocytochemical staining was used to map the localization of the EVH1 domain within the Rat2 cells.

Methods

For descriptions of molecular cloning, retroviral packaging, infection, FACS sorting, cell culture, and immunofluorescence microscopy. see Example 1, Methods Section.

EGFP-EVH1 Construct Production

The EGFP-EVH1 construct was created by amplifying a portion of the EGFP-Mena construct (encoding EGFP and Mena amino acids 1–117 of SEQ ID NO: 2) and substituting it for the full-length version in the retroviral construct. For description of basic EGFP-Mena construct production see Example 1, Methods Section.

Results

When the Rat2 cells were examined for F-actin, GFP, and vinculin signal by immunocytochemical staining, the EVH1 domain alone directed GFP localization to both focal adhesions and the leading edge. Focal adhesion and leading edge EGFP-EVH1 signal was not as robust as it was with the full-length EGFP-Mena, perhaps because these molecules cannot multimerize through the EVH2 domain and increase relative signal strength. This construct may also be in competition for limited binding sites with more avid, multimerized endogenous Ena/VASP complexes. It should also be noted that this construct, unlike full-length EGFP-Mena, is detected in the nucleus. It may lack a nuclear exclusion signal that is present in the full-length protein or is simply small enough to enter the nucleus through diffusion. Expression of untagged EGFP resulted in diffuse cytosolic and nuclear GFP signal. These results indicate that, in fibroblasts, the EVH1 domain is sufficient to direct leading edge localization as well as for focal adhesion targeting. The EVH1 domain was localized in the focal adhesions and the leading edge and appears to be the component of the Mena molecule that is responsible for leading edge localization.

Example 6

Introduction

Figure 5A:
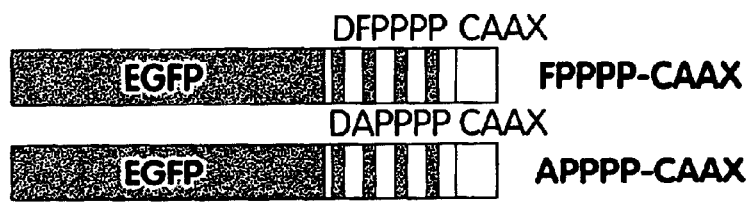
FIG. 5: Constitutive targeting of Ena/VASP proteins to the plasma membrane inhibits cell motility. (a) Schematic diagram of membrane targeting constructs (b) Immunofluorescence analysis of FPPPP-CAAX (SEQ ID No.: 7) and APPPP-CAAX (SEQ ID NO.: 8) expressing cells. (c) Box and whisker plots of cell speed (ANOVA p-value<0.0001).

The results of the FPPPP-mito (SEQ ID NO: 3) and FPPPP-cyto (SEQ ID NO: 3) experiments (Examples 2–4) indicated that either the cytosolic or leading edge pools of Ena/VASP proteins were responsible for the changes in motility observed in these experiments. To distinguish between these possibilities, the EGFP-FPPPP (SEQ ID NO: 3) construct was modified to include the lipid modification domain (CAAX box, SEQ ID NO: 6) from H-ras (Choy, E., Chiu, V. K., Silletti, A, Feoktistov, M., Morimoto, T., Michaelson, D., Ivanov, I. E., and Philips, M. R. (1999). Endomembrane trafficking of ras: the CAAX motif targets proteins to the ER and Golgi. Cell 98, 69–80). This construct directs the EVH1 binding sites to the inner leaflet of the plasma membrane. Constructs that contained either intact repeats (FPPPP-CAAX, SEQ ID NO: 7) or mutant repeats (APPPP-CAAX, SEQ ID NO: 8), as illustrated in FIG. 5a, were introduced in parallel into Rat2 cells by retroviral transduction. Immunocytochemical staining was used to map Mena and GFP localization.

Methods

For descriptions of molecular cloning, retroviral packaging, infection, FACS sorting, cell culture, and immunofluorescence microscopy. see Example 1, Methods Section.

CAAX-Construct Production

FPPPP-CAAX (SEQ ID NO: 7) and APPPP-CAAX (SEQ ID NO: 8) contain the same fragment as the cyto constructs, but also contains a C-terminal extension that encodes the final 20 amino acids of the human h-Ras protein. (See Example 4, Methods Section for cyto construct details).

Results

Figure 5B:
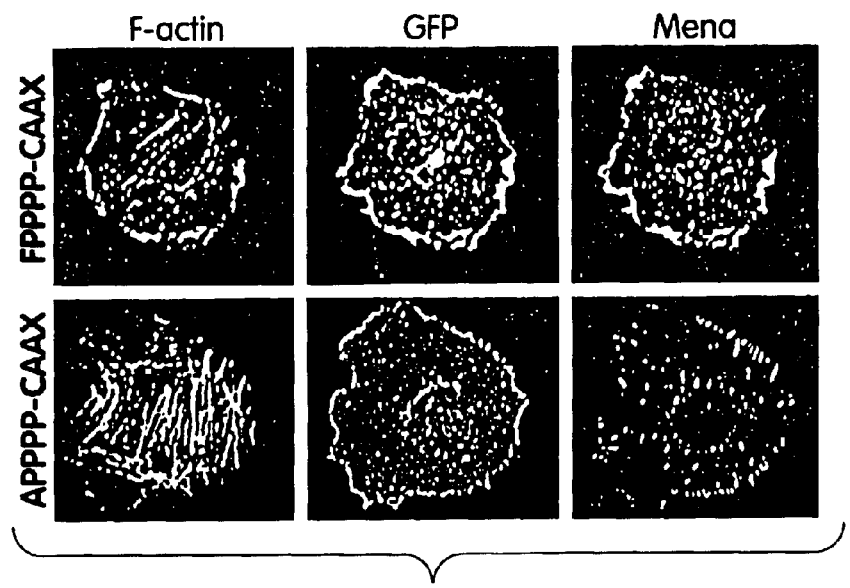
Figure 5C:
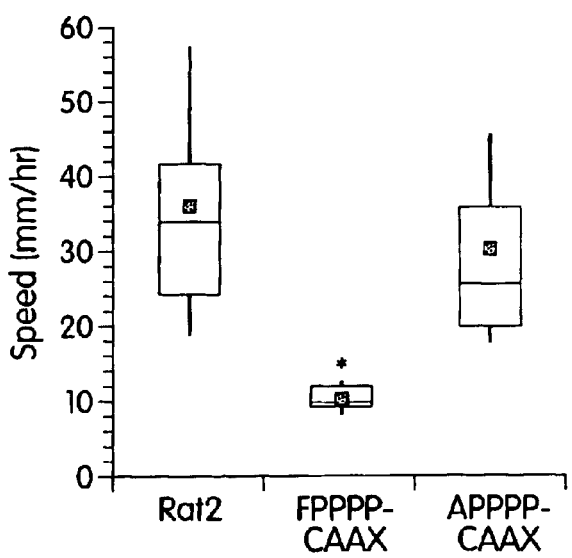
Figure 6A:
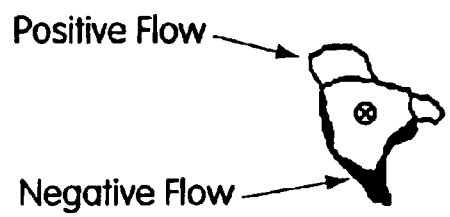
FIG. 6: Protrusion and refraction, independent of cell translocation, positively correlates with speed. (a) Diagram illustrating positive and negative membrane flow. The outlines of the same cell in two adjacent frames are overlaid, new areas of protrusion are indicated in green, areas of retraction are in red. (b) Box and whisker plot of average flow per 10 minute time period. Average flow calculated by averaging the absolute values of positive and negative flow and is expressed as a % of total cell area from the first frame (ANOVA p-value <0.0001). FPPPP is SEQ ID NO.: 3. FPPPP-CAAX is SEQ ID NO.: 7.

When these cells were examined for Mena and GFP localization by immunocytochemistry, all the Mena was re-distributed to the plasma membrane in the FPPPP-CAAX (SEQ ID NO: 7) cells, but not in those expressing APPPP-CAAX (SEQ ID NO: 8; FIG. 5b). F-actin distribution remained largely unchanged in the FPPPP-CAAX (SEQ ID NO: 7) cells, although these cells showed some increased propensity to form ruffles. When these cells were analyzed by the time-lapse videomicroscopy assay (see Example 1, Methods Section), the FPPPP-CAAX (SEQ ID NO: 7) cells exhibited almost no ability to translocate (FIG. 5c), but the speed of the APPPP-CAAX (SEQ ID NO: 8) cells was statistically indistinguishable from the uninfected control cells (FIG. 6c). Although the FPPPP-CAAX (SEQ ID NO: 7) cells could attach and spread with apparently normal kinetics, they very rarely adopted the polarized morphology characteristic of a motile cell. Interestingly, the one exception to this was immediately following mitosis, when these cells could polarize (perpendicular to the plane of division) and migrate a short distance. These results indicate that Ena/VASP proteins inhibit motility when directed to the plasma membrane.

Example 7

Introduction

The dramatic changes in cell motility observed by changing the level or subcellular distribution of Mena and VASP suggested that these proteins play a role in regulating membrane extension. To investigate this possibility, the digitized movies of the various cell populations were compared for the parameter of cell shape change.

Methods

The measurement of shape change involves comparing the outlines of a cell in adjacent frames of a movie. Newly protruded area (membrane extension) is termed positive flow, and membrane area retracted from the previous frame is negative flow (top and bottom, respectively, FIG. 6a). When averaged over the course of the movie, positive flow nearly always matches negative flow because the cells don't appreciably change volume or extent of spreading. The average of the absolute values of positive and negative flow describes a cell's ability to shape change (i.e. the sum of membrane extension and retraction). The centroid positions of the cells were fixed in place during this calculation to derive a value independent of cell translocational speed. This is an important aspect of cell shape analysis because it separates translocation from protrusion/retraction. The average flow-per-unit-time was compared across the various cell populations tested. For additional details on time-lapse videomicroscopy see Example 1, Methods Section.

Figure 6B:
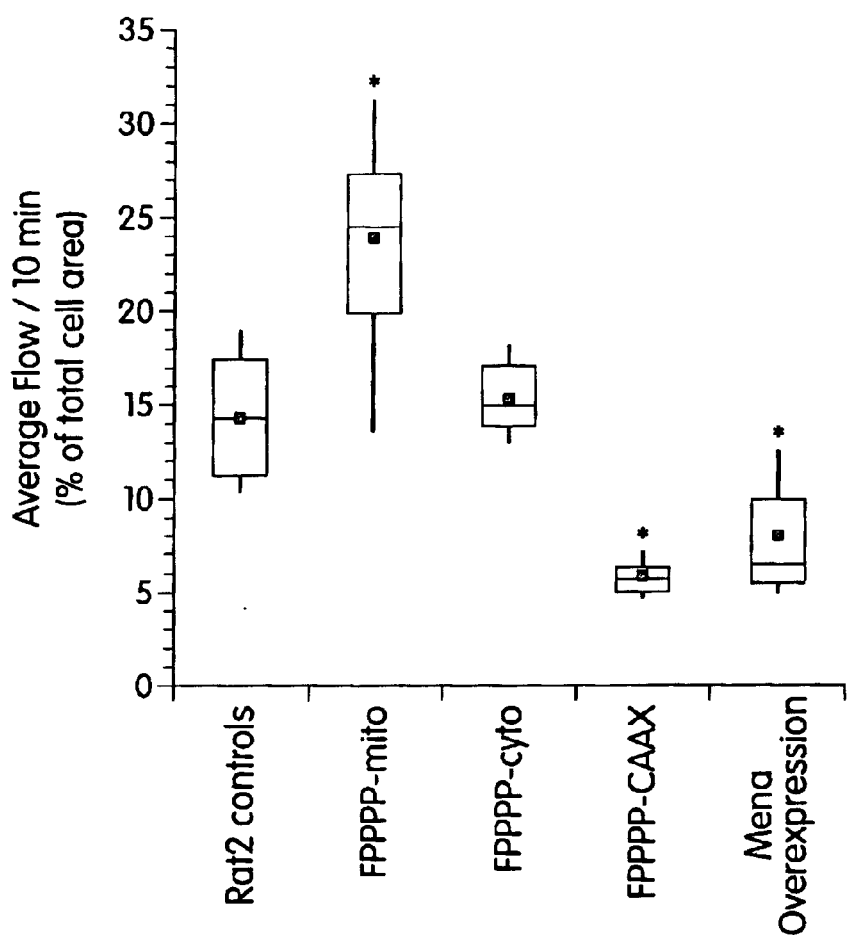

Results When the average flow per unit time was compared across the various cell populations tested, a striking positive correlation was observed with translocational speed (FIG. 6b). The cells expressing FPPPP-mito (SEQ ID NO: 3) moved the fastest and changed shape most dramatically over time, and the slow-moving EGFP-Mena overexpressing cells and FPPPP-CAAX (SEQ ID NO: 7) cells changed shape the least. These data indicate that the rate of membrane extension and retraction is retarded by Ena/VASP proteins, and that this effect correlates with the effect on cell speed.

Example 8

Introduction

To demonstrate that Ena/VASP proteins act to negatively regulate cell speed, cells lacking all Ena/VASP proteins were analyzed. To isolate such Ena/VASP protein-deficient cells, mice carrying deletions of Mena and VASP were utilized to generate double homozygous mutant embryos from which populations of embryonic fibroblasts were cultured. The MV fibroblast populations were stained with an antibody against EVL, the remaining known Ena/VASP protein, and both EVL expressing and non-expressing cells were observed. Clonal derivatives of the original MV population were screened to identify cell lines that lacked detectable EVL expression. A representative line, MV$^{D7}$, was selected for further characterization. Western blot analysis of MV$^{D7}$ cells confirmed that these cells lack detectable levels of Mena, VASP and EVL.

If the increased speeds observed in the cells expressing the FPPPP-mito (SEQ ID NO: 3) construct were due to specific effects on Ena/VASP proteins, then cells lacking Ena/VASP proteins should be refractory to expression of FPPPP-mito (SEQ ID NO: 3). To test this hypothesis, populations of MV$^{D7}$ expressing the FPPPP-mito (SEQ ID NO: 3) construct were generated and analyzed by time-lapse videomicroscopy.

If the absence of Ena/VASP proteins in focal adhesions and the leading edge results in increased cell speeds, then rescue of the MV$^{D7}$ line by expression of Mena should reduce cell speeds. To create an appropriate population of rescued cells, MV$^{D7}$ cells were infected with the retrovirus to drive expression of EGFP-Mena and sorted by FACS to create a population of MV$^{D7}$ cells that express moderate levels of Mena (MV$^{D7}$/EGFP-Mena).

Methods

For mito-construct production see Example 2, Methods Section. For descriptions of molecular cloning, retroviral packaging, infection FACS sorting, Cell culture, immunofluorescence microscopy, quantitative western blots, and time-lapse videomicroscopy see Example 1, Methods Section.

Derivation and culturing of MV$^{D7}$ cells

E9.5 embryos from crosses of Mena/VASP compound heterozygous parents were sterilely dissected and dissociated by incubation in trypsin/EDTA solution for 25 minutes at 37° C. To facilitate cell line derivation, the embryos harbored a transgene that expresses a temperature-sensitive version of the Large-T antigen. Embryonic tail clips were collected for genotyping prior to dissociation. Dissociated cells were pelleted, resuspended in Immorto media (DME with 15% FCS, pen/strep, L-glutamine and 50 U/mL of recombinant mouse interferon-gamma (Life Technologies, Inc.)), plated, and allowed to spread overnight. After one passage, cells were sorted by FACS into the wells of a 96-well plate coated with collagen I (Becton-Dickinson) containing 80 μL of fibroblast-conditioned Immorto media. The MV$^{D7}$ line was grown at 32° C. in Immorto media and infected with retroviruses as in Rat2 cells (see Example 1, Methods).

Results

Figure 7:
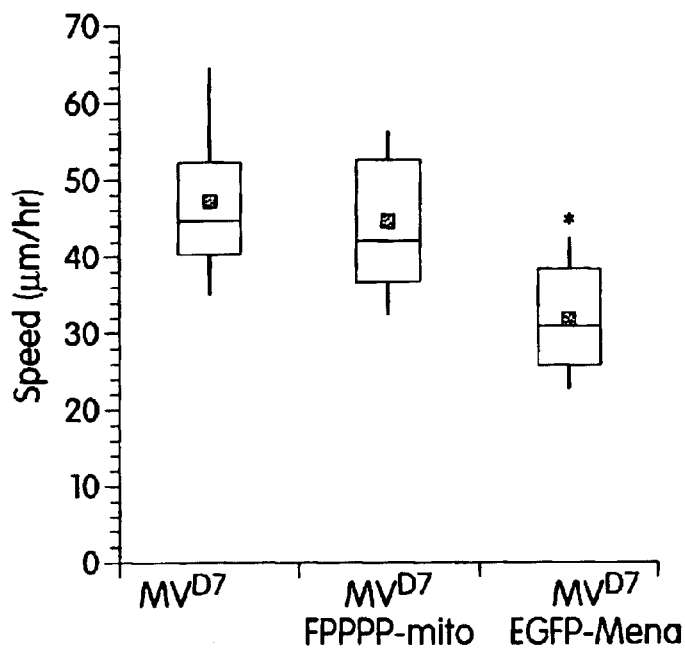
FIG. 7: Complementation of Ena/VASP-deficient cells slows motility. Box and whisker plots of cell speed of $MV^{D7}$ and $MV^{D7}$/EGFP-Mena cells (ANOVA p-value< 0.0001). FPPPPP is SEQ ID NO.: 3.

The speeds of MV$^{D7}$/FPPPP-mito (SEQ ID NO: 3) cells were statistically indistinguishable from those of the parental MV$^{D7}$ line, which indicates that the phenotype induced by expression of FPPPP-mito (SEQ ID NO: 3) results from a specific perturbation of Ena/VASP proteins. FACS analysis indicated that, on an average per cell basis, the MVD$^{D7}$/EGFP-Mena cells express a level of EGFP-Mena roughly equivalent to that of the "low" population of EGFP-Mena overexpressing Rat2 cells presented in FIG. 1. Because the amount of EGFP-Mena in the "low" population is similar to the amount of endogenous Mena in Rat2 cells, the MV$^{D7}$/EGFP-Mena cells express Mena at a level roughly comparable to that found in Rat2 fibroblasts. The MV$^{D7}$ and MV$^{D7}$/EGFP-Mena cell lines were analyzed by immunofluorescence staining with probes to vinculin and F-actin and examined to verify proper distribution of EGFP-Mena. No gross differences were observed between the two cell lines, indicating that deficiency of all Ena/VASP proteins has no effect on the appearance of focal adhesions or the distribution of F-actin. The migration rates of the MV$^{D7}$ and MV$^{D7}$/EGFP-Mena cell lines were analyzed by time-lapse videomicroscopy. The MV$^{D7}$ cells migrated significantly faster than the MV$^{D7}$/EGFP-Mena cells, indicating that cell speeds are reduced by complementation of the Ena/VASP-deficient cells with Mena. The results are shown in FIG. 7. When combined with the data from Rat2 cells expressing the FPPPP-mito (SEQ ID NO: 3) construct, these results provide compelling evidence that cell motility rates are increased in the absence of Ena/VASP proteins.

Example 9

Introduction

To determine the mechanism of action through which Ena/VASP proteins alter cell motility, the interaction between Ena/VASP proteins and actin was examined. Actin polymerizes to form branched filaments which can be long or short. Additional actin monomers are added to the barbed end of the actin filament during the polymerization process. When the barbed end is contacted with a capping protein, the filament formation stops. The following experiments were designed to determine the role of Ena/VASP in actin polymerization.

1. Effect of cytochalasin D on Ena/VASP localization.

Methods

Rat2 cells were cultured and examined by immunofluorescence microscopy as described in Example 1, Method Section. For this experiment, the cells were incubated with 150 nM cytochalasin D. (Sigma-Aldrich, St. Louis, Mo.). The effect of cytochalasin D on Ena/VASP localization and cell movement was examined.

Results

When cytochalasin D is incubated with a cell it interacts with the free barbed ends of the actin. It was found in the experiments that localization of Ena/VASP was altered in response to cytochalasin D treatment. The Ena/VASP proteins were shifted away from the leading edge. Since the cytochalasin D blocked the free barbed ends, it was concluded that free barbed ends of actin filaments were necessary for localization of Ena/VASP to the leading edge of the cell.

2. Actin Filament Capture Assay.

Methods 2.8 micrometer paramagnetic beads (Dynal Biotech Inc., Lake Success, N.Y.) were coated with FPPPP peptide (SEQ ID NO: 3). The beads were incubated with VASP to produce a coating of VASP on the surface of the bead. The VASP coated beads were then incubated with pre-formed actin filaments or with actin filaments that were pre-incubated with capping protein (10 nM). Filaments that were pre-incubated with capping were not captured by VASP beads, whereas uncapped filaments were. The ability of the beads to capture actin was measured.

Results

The beads that were pre-incubated with barbed ends failed to capture actin. The beads that were not subjected to the pre-incubation step captured the actin. These results are consistent with and support the results described above demonstrating that VASP interacts with the barbed ends of actin.

3. Effect of cytochalasin D dosage on cell motility.

Methods

Rat 2 cells were exposed to 0, 5 nM, 25 nM, 50 nM, or 500 nM cytochalasin D and motility was measured. One set of cells received no cytochalasin D. Other cells received a low dose of cytochalasin D (e.g. 5 nM or 25 nM) or a high dose of cytochalasin D. (e.g. 500 nM) The motility of the treated cells was assessed using the motility assay described above.

Results

An interesting biphasic result was observed; it was found that cell speed was increased at 25 nM, but decreased at 500 nM. Cells expressing Ena/VASP localized at the leading edge of the cell migrated slowly as expected. Cells exposed to high levels of cytochalasin D also migrated slowly as expected. The cells receiving a low dose of cytochalasin D, however, actually demonstrated in increase in migration rate compared to the untreated cells and the cells treated with high dosages of cytochalasin D. It is believed that at the low dosage of cytochalasin D only a fraction of the barbed ends were capped leading to a decrease in average filament length, and that these shorter filaments get incorporated into structures that more effectively move the cells forward. Presumably the high doses of cytochalasin D blocked all or nearly all of the barbed ends leading to a block of actin polymerization and consequently poor cell movement. Because the Ena/VASP proteins help elongate filaments by protecting them from capping proteins, the low-dose cytochalasin D treatment mimics the depletion of Ena/VASP protein in either the FPPPP-mito (SEQ ID NO.: 3) expressing cells or in the $MV^{D7}$ cells, which are both fast moving cells.

4. Effect of Ena/VASP on the formation of actin filaments.

Methods

Cells positive for Ena/VASP and cells negative for Ena/VASP were examined. The actin filaments present in the leading edge of the these two classes of cells were examined by electron microscopy. For this study the cells used were: Rat2 cells (controls), Rat2/FPPPP-mito (SEQ ID NO.: 3) (fast), Rat2/FPPPP-CAAX (SEQ ID NO.: 7), Rat2/EGFP-Mena (high) (both CAAX (SEQ ID NO.: 6) and EGFP-Mena are slow). The fast-moving cells have short, highly branched actin filaments whereas slow-moving cells have long, unbranched actin filaments.

Results

It was discovered that cells expressing Ena/VASP produced long chain actin filaments. As described in the experiments above, it was concluded that Ena/VASP associates with the barbed end of the actin and permits filament elongation. Based on these results, it is believed that Ena/VASP proteins block capping of the actin filaments and allow elongation to continue to form long actin filaments. The actin filaments in the Ena/VASP negative cells, however, were short branched chains. In the absence of Ena/NASP, the capping of actin occurred preventing further elongation of the chains. Thus, long actin filaments associated with the localization of Ena/VASP result in slower cellular migration. The formation of short branched actin is associated with faster migration rates.

Example 10

Introduction

To determine which portions of the Ena/VASP proteins were responsible for cellular localization and function, several mutants of Ena/VASP proteins were generated. The localization and functional properties of the cells in which the mutant proteins were expressed were examined.

Methods

Several mutations were introduced into the gene encoding the Mena protein using routine molecular biology techniques. Briefly, the novel Mena mutants were generated by using mutagenic PCR primers designed to generate missense mutations in the Mena open reading frame. For the small deletions of conserved Ena/VASP regions, PCR reactions proceeded in two sequential steps. First, two PCR reactions were run in parallel, using wild-type Mena as template, to generate two fragments of DNA encoding the regions 5' and 3' to the targeted deletion. Primers were designed to include an overlap to permit a second PCR reaction using the two fragments as a heterodimeric template for the generation of the novel structural variant of Mena. That final PCR product was cloned into a plasmid, and confirmed by DNA sequencing and RFLP analysis. For the point mutations, mutagenic primers were used to amplify the entire vector (pBSII) and insert. The original template DNA was then digested by the methylation sensitive restriction endonuclease DpnI, and the product of that reaction was transformed into bacteria. DNA sequencing confirmed the mutations. The constructs were introduced into Rat2 cells by retroviral transduction and immunocytochemical staining was used to map the localization of the wild type and mutant proteins. The methods were carried out as described above in Example 1. Rates of cell migration were also examined as described above in Example 1, for whole cells. The rate of Listeria movement was also measured, using the following method.

MVD7 cells were seeded onto a Bioptics dish the night before an experiment, and Listeria was also cultured overnight taking care to not over saturate the bacterial culture. MVD7 cells were then exposed to Listeria. The Bioptics dishes were centrifuged at 500×g for 3 min in a swinging bucket centrifuge to force the bacteria up against the MVD7 cells. The cells were then incubated for 1.5 hrs at 37° C. The plates were washed 3 times with media to remove bacteria not associated with cells. Bacteria were then viewed with 100x phase contrast microscopy. Time-lapse movies were recorded and speeds were quantitated with DIAS software.

Results

Results

Figure 8:
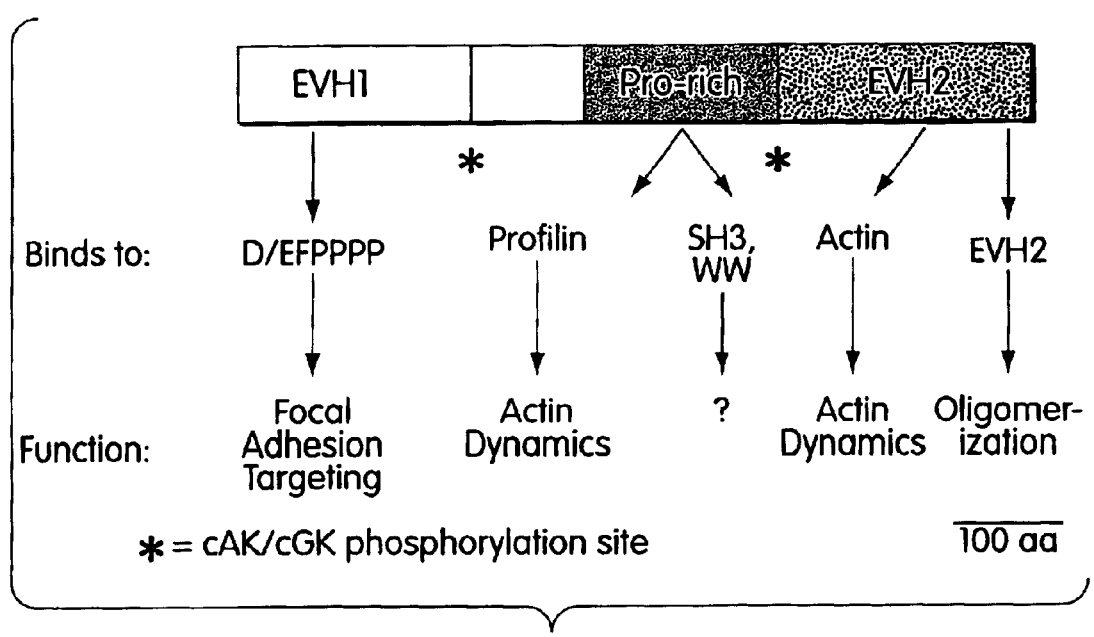
FIG. 8: Known properties of Ena/VASP Proteins. Schematic diagram illustrating conserved domains within the Ena/VASP protein family. D/EFPPPP is SEQ ID NO.: 1.

FIG. 8 is a schematic diagram depicting the known properties of Ena/VASP proteins. The properties conserved among the known Ena/VASP proteins include an EVH1 domain which is known to bind to D/EFPPPP (SEQ ID No.: 14). The EVH1 domain is believed to play a role in focal adhesion targeting. Another conserved domain known as the proline rich domain is also shown in FIG. 8. The proline rich domain binds to profilin and SH3, WW. This domain is believed to play a role in actin dynamics. A third conserved domain is referred to as EVH2. The EVH2 domain binds to actin and is involved in the mediation of actin dynamics and oligomerization. In addition to the conserved domains, two phosphorylation sites are highly conserved within Ena/VASP proteins. These phosphorylation sites are designated in FIG. 8 with a *.

Figure 9:
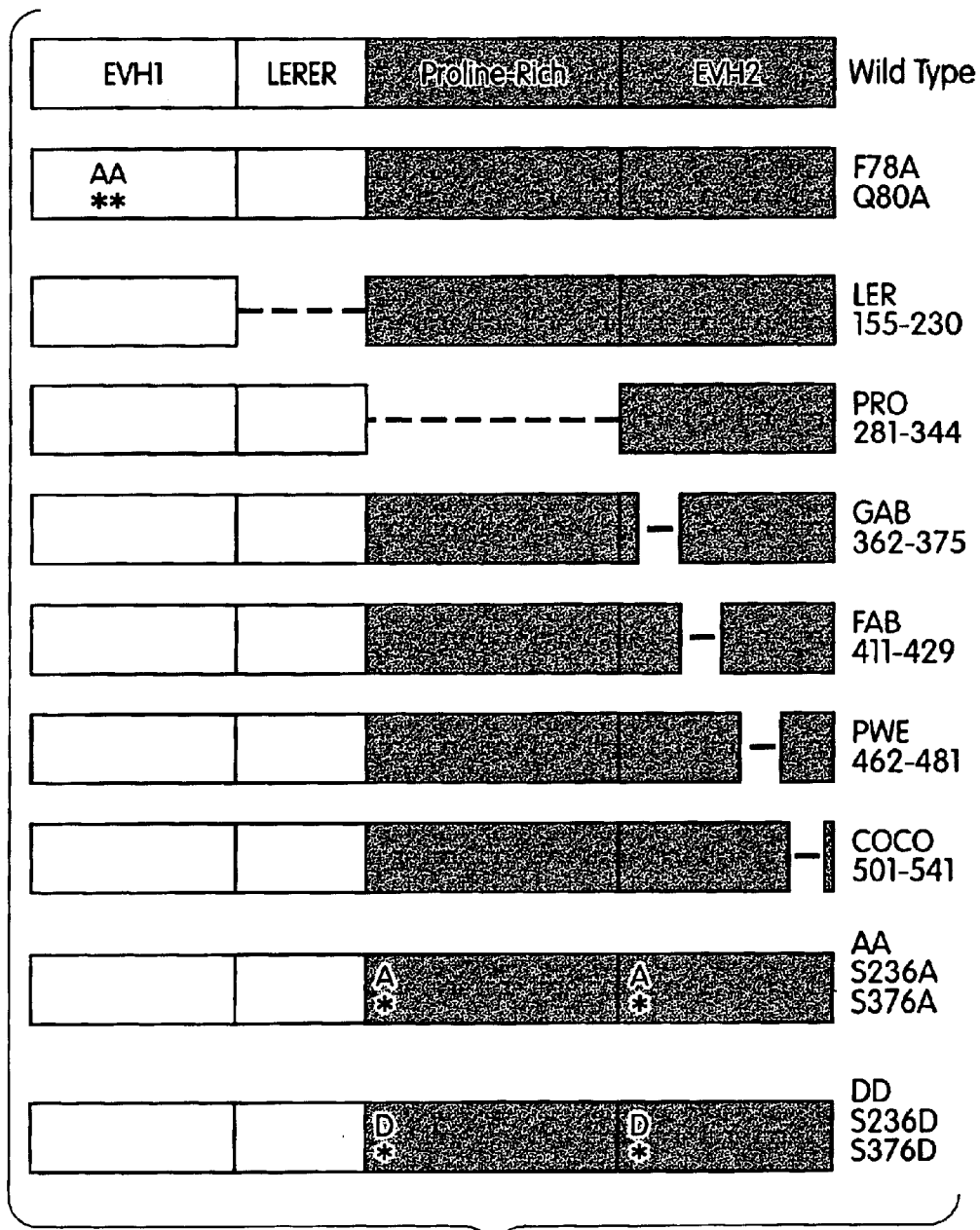
FIG. 9: Mena Mutants. Diagram illustrating the mutations made to the Mena protein.

FIG. 9 shows a schematic of the mutants produced and tested for localization and activity. The protein depicted by the top bar of FIG. 9 is the wild type Mena. The protein, referred to as F78AQ80A, directly below the wild type involves a mutation within the EVH1 domain of amino acids 78 and 80 ( phenylalanine to alanine and glutamine to alanine respectively). The next protein down, which is referred as LER, involves a deletion of amino acids 155–230. The protein referred to as PRO involves a deletion of amino acids 281–344, which is the proline rich domain. The proteins referred to as GAB, FAB, PWE, and COCO involve deletions of amino acids 362–375, 411–429, 462–481, and 501–541 of the EVH2 domain, respectively. The protein referred to as AA involves two point mutations in which a serine residue was replaced with an alanine at site 236 and 376. The protein referred to as DD involves the substitution of an aspartate for the same two serine residues as in the AA mutants.

Figure 10:
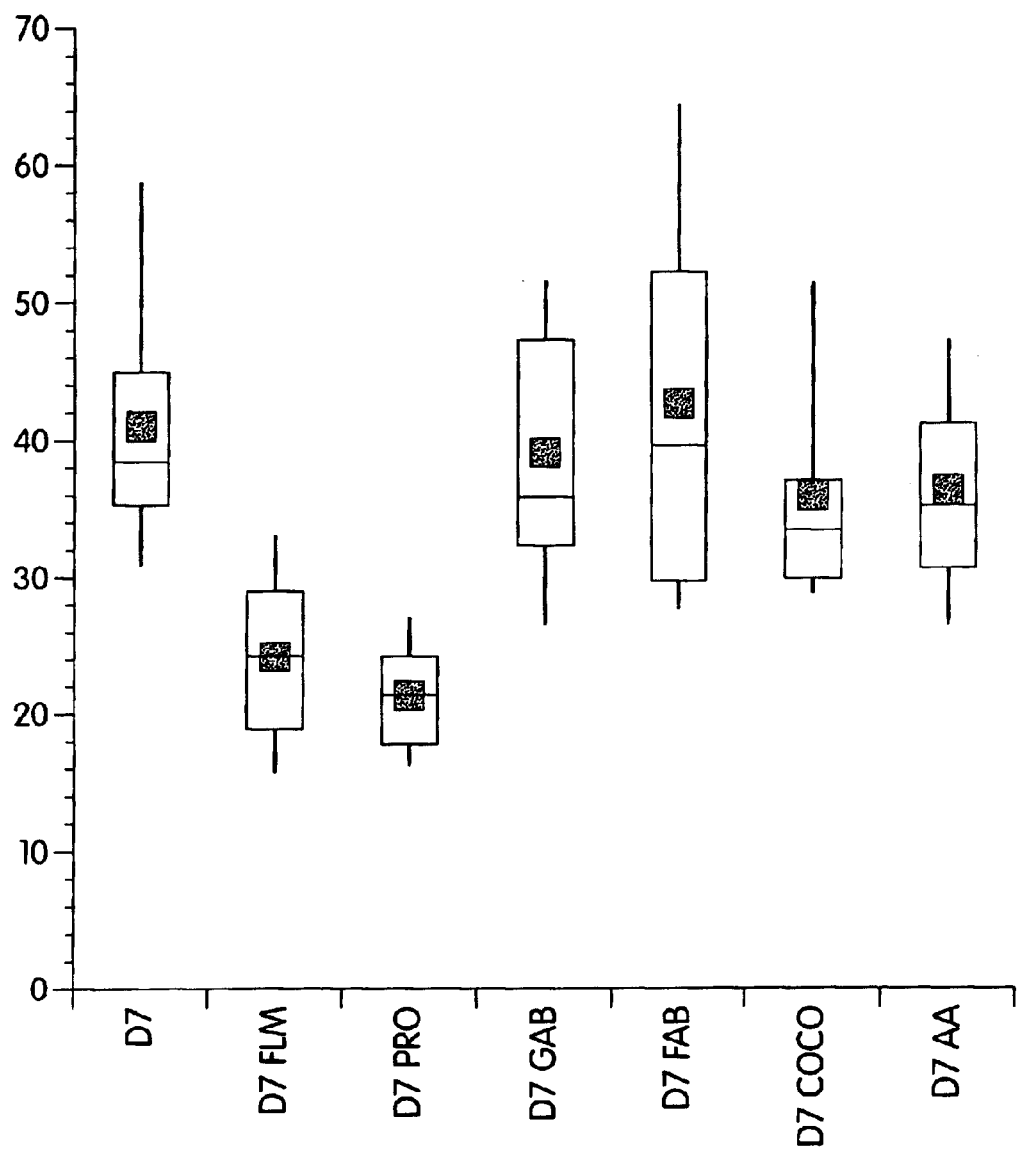
FIG. 10: Effect of specific mutations within Mena on whole cell motility. Box and whisker plots depicting cell speed resulting form the introduction of mutants described in FIG. 9 into cells.

The proline rich mutant referred to as PRO also demonstrated interesting results. Localization of Ena/VASP to the leading edge in the PRO mutant appeared normal. Additionally, the motility of cells transformed with the PRO mutant was not altered from that of the control wild type cells (FIG. 10, D7-PRO). Interestingly, however, the PRO mutant (GFP-Mena (pro) high) dramatically reduced Listeria motility (FIG. 11) compared to the mena/VASP null cells (GFP-mena high). The data suggests different control points within the Ena/VASP proteins for the regulation of whole cell movement versus Listeria movement.

Figure 11:
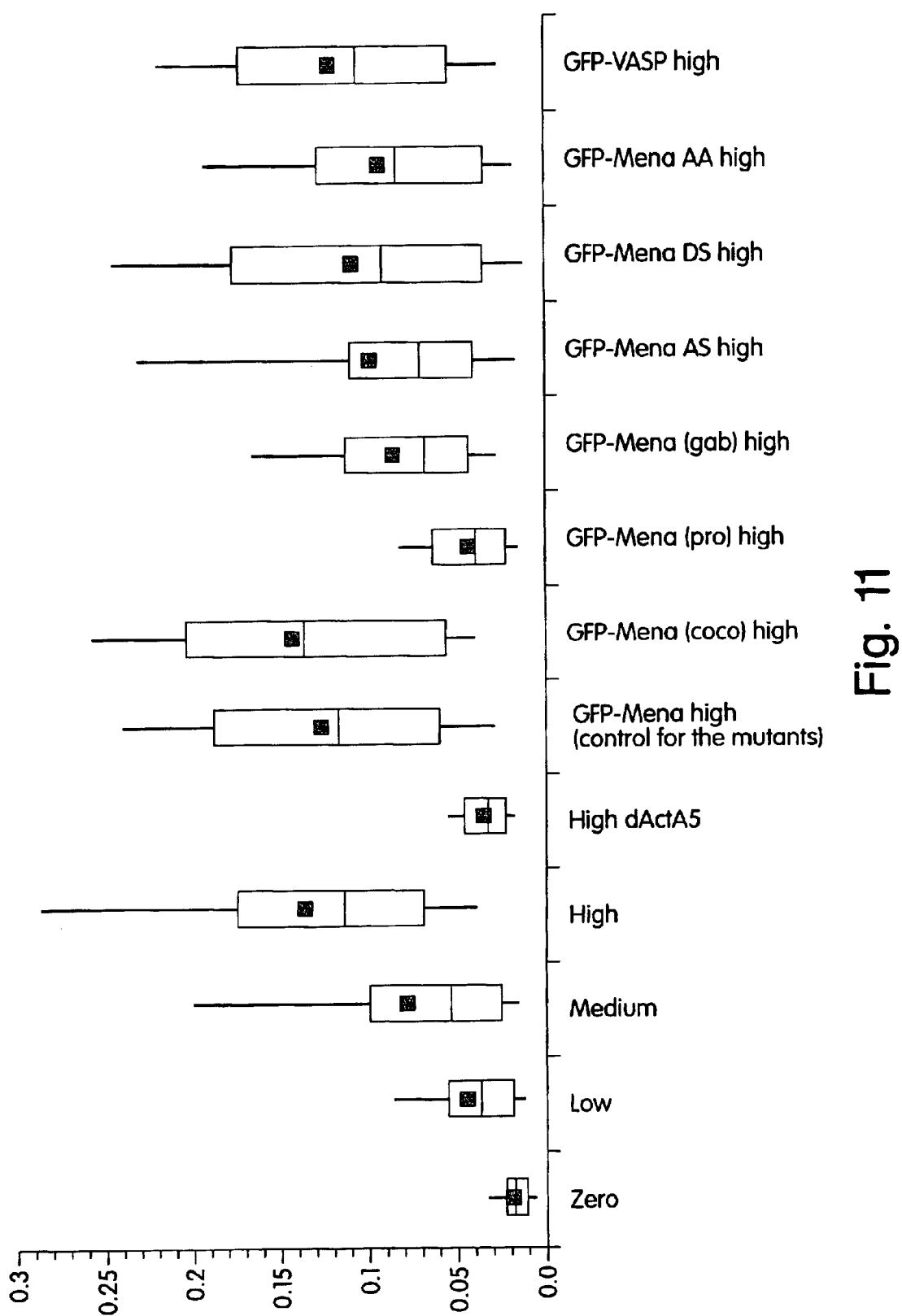
FIG. 11: Effect of specific mutations within Mena on Listeria motility. Box and whisker plots of depicting Listeria speed resulting form the introduction of mutants described in FIG. 9 into Listeria.

Mutation of one or both of the conserved phosphorylation sites within the Ena/VASP proteins also provided important information about the structure/function relationship. Deletion of the phosphorylation sites which are highly conserved in the Ena/VASP proteins resulted in normal localization of Ena/VASP. Thus, phosphorylation does not play a role in localization of Ena/VASP to the leading edge. Deletion of the phosphorylation sites, however, knocked out the activity of Ena/VASP in both the whole cell motility and the Listeria assay. Cells transformed with the mutants lacking the two conserved phosphorylation sites (referred to in FIG. 10 as D7AA) moved much more quickly than cells transformed with the wild type construct (referred to FIG. 10 as D7FLM). As shown in FIG. 11, this double mutation (referred to in the figure GFP-Mena AA high) had slightly reduced motility compared to the control (GFP-Mena high). In FIG. 11 the designations zero, low, medium, and high refer to the amount of Ena/VASP protein expressed in the cell.

The differences in Listeria speed are quite significant and quite dependent on Ena/VASP proteins. This observation is accentuated by the "high dAct A5" experiments, which involved MVD7: "high" EGFP-Mena expressing cells infected with a strain of Listeria carrying a mutant ActA allele, dAct A5, that can not bind to Ena/VASP proteins (it is missing the four FPPPP repeats (SEQ ID NO.: 3) necessary for the protein-protein interaction). In contrast, wild-type Listeria are mobile in MVD7 cells that express EGFP-Mena, mutations that affect Listeria's ability to recruit Ena/VASP proteins block Listeria movement in MVD7 cells expressing EGFP-Mens.

Example 11

Introduction

To demonstrate the effect of Ena/VASP proteins in an in vivo setting, an animal model for neuronal cell differentiation and migration was examined. In developing embryos neuronal cells divide and migrate to a predetermined position where they ultimately differentiate and form the brain. The extent of migration of each cell depends on the time that the cell is created, with the earliest cells migrating the least difference and the newest cells migrating the farthest. The effect of Ena/VASP proteins was studied in this model of the developing brain.

Methods

The Ena/VASP null cell as described above in Example 8 were injected into the brain of developing murine embryos. After development, the brains were examined for the presence of cells derived from the Ena/VASP null phenotype. The position of these cells in the developed brain was examined relative to cells expressing normal Ena/VASP proteins.

Results

Figure 12:
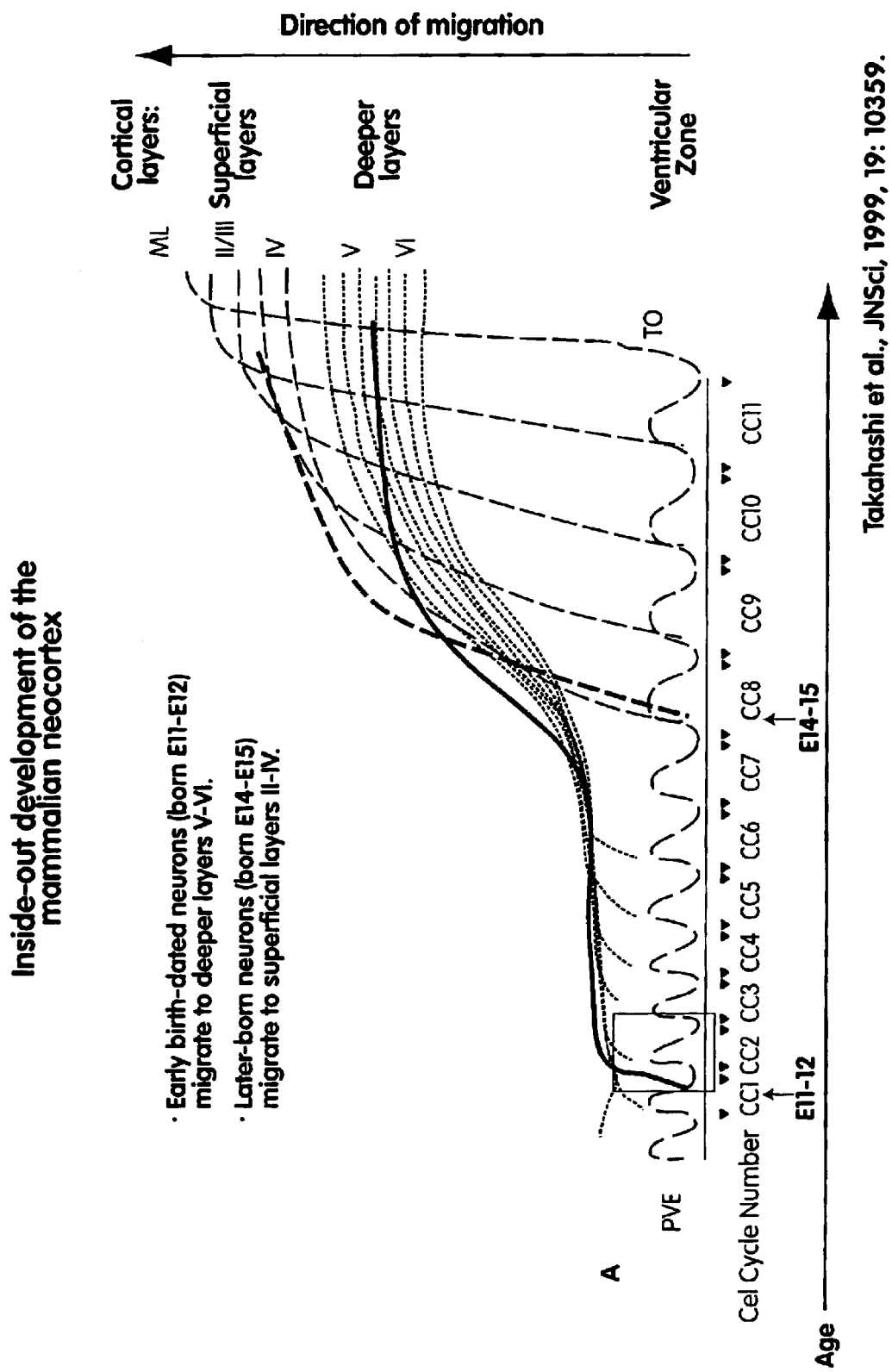
FIG. 12: Normal neuronal development and migration in the brain. Schematic diagram depicting that the cells being formed first migrate the shortest amount of distance and differentiate at that site. The set of cells developing next migrate past the first set of cells and remain positioned above the early cells in the brain. The last cells to develop migrate the furthest and form the outer most regions of the brain.

FIG. 12 is a schematic diagram depicting the cellular development and migration resulting in the formation of the brain. At the far left of the diagram, the cells being formed first migrate the shortest amount of distance and differentiate at that site. The set of cells developing next migrate past the first set of cells and remain positioned above the early cells in the brain. The last cells to develop migrate the furthest and form the outer most regions of the brain.

Figure 13:
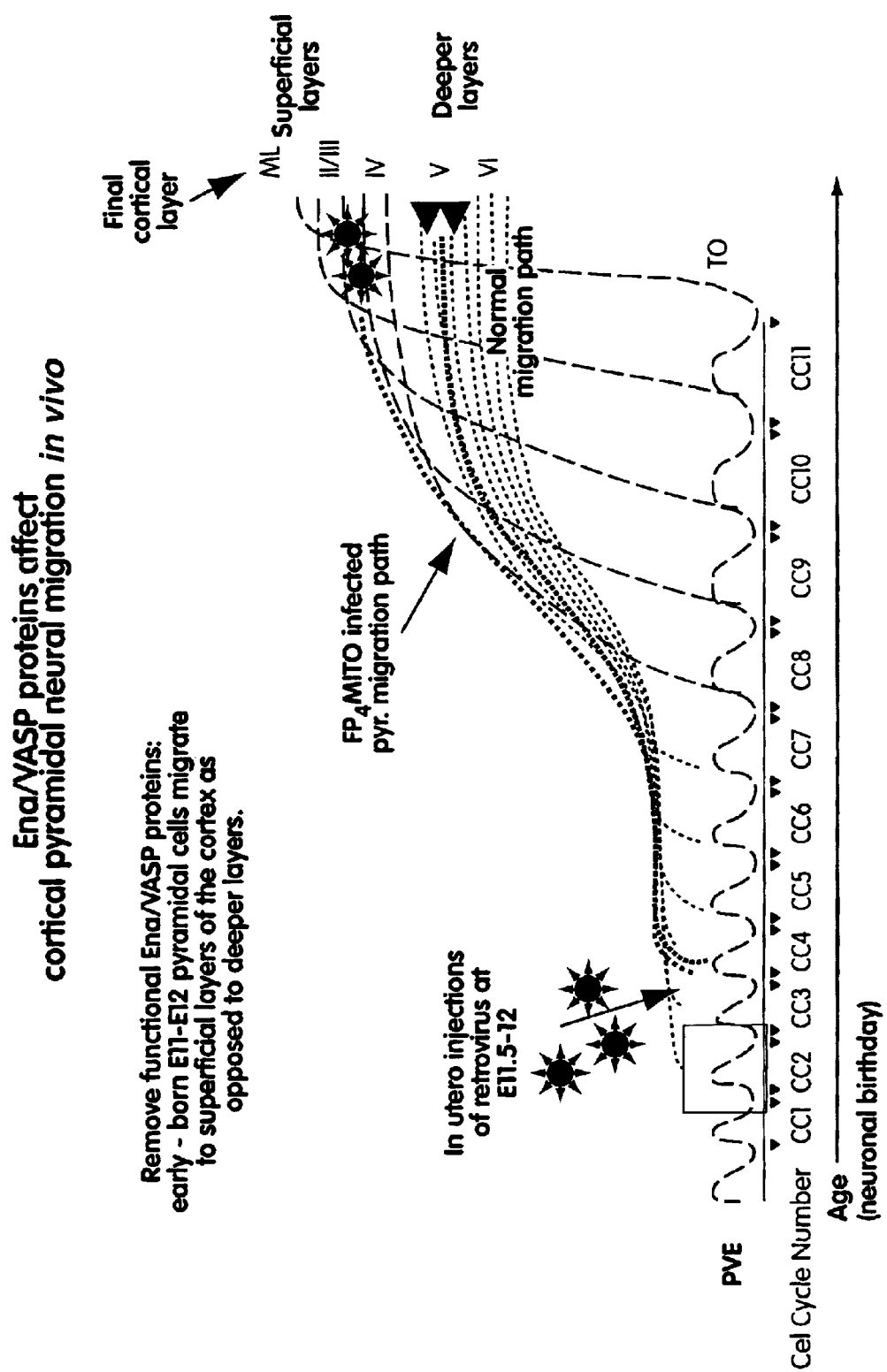
FIG. 13: Neuronal development and migration in the brain with Ena/VASP null cells. Schematic diagram depicting cells which were Ena/VASP null migrate the furthest and are positioned at the top portions of the brain. Cells developing at the same time as the Ena/VASP null cells migrate to lower portions of the brain.

FIG. 13 is a schematic diagram depicting the results of the experiment described above. The cells which were Ena/VASP null migrated the furthest and were positioned at the top portions of the brain. Cells developing at the same time as the Ena/VASP null cells migrated to lower portions of the brain. These results demonstrate that the removal of functional Ena/VASP protein from developing neurons enhances their migration in an in vivo setting.

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. All references, patents and patent publications that are recited in this application are incorporated in their entirety herein by reference.

We claim:

1. A method for identifying an Ena/VASP activator or inhibitor, comprising:
   contacting a mammalian cell with a putative Ena/VASP activator or inhibitor,
   determining the effect of the putative Ena/VASP activator or inhibitor on cell migration, and
   identifying the putative Ena/VASP activator or inhibitor as an Ena/VASP activator when the mammalian cell has a decreased rate of migration or as an Ena/VASP inhibitor when the mammalian cell has an increased rate of migration with respect to an untreated control mammalian cell.

2. The method of claim 1, wherein the putative Ena/VASP activator or inhibitor is identified as an Ena/VASP activator.

3. The method of claim 1, wherein the putative Ena/VASP activator or inhibitor is identified as an Ena/VASP inhibitor.

4. The method of claim 1, wherein the putative Ena/VASP activator or inhibitor is an oligonucleotide.

5. The method of claim 1, wherein the putative Ena/VASP activator or inhibitor is a peptide.

6. The method of claim 1, wherein the putative Ena/VASP activator or inhibitor is a peptide mimetic.

7. The method of claim 1, wherein the putative Ena/VASP activator or inhibitor is selected from a library.

* * * * *